US008669282B2

(12) United States Patent  (10) Patent No.: US 8,669,282 B2
Zicker et al.  (45) Date of Patent: *Mar. 11, 2014

(54) COMPANION ANIMAL COMPOSITIONS INCLUDING LIPOIC ACID AND METHODS OF USE THEREOF

(75) Inventors: Steven C. Zicker, Lawrence, KS (US); Nolan Zebulon Frantz, Topeka, KS (US)

(73) Assignee: Hill's Pet Nutrition, Inc., Topeka, KS (US)

(*) Notice: Subject to any disclaimer, the term of this patent is extended or adjusted under 35 U.S.C. 154(b) by 837 days.

This patent is subject to a terminal disclaimer.

(21) Appl. No.: 12/319,287

(22) Filed: Dec. 30, 2008

(65) Prior Publication Data

US 2009/0182032 A1 Jul. 16, 2009

Related U.S. Application Data

(63) Continuation-in-part of application No. 11/154,210, filed on Jun. 16, 2005, now Pat. No. 8,592,478, which is a continuation of application No. 09/978,132, filed on Oct. 16, 2001, now Pat. No. 6,914,071, which is a continuation-in-part of application No. 09/922,660, filed on Aug. 6, 2001, now abandoned.

(60) Provisional application No. 60/253,448, filed on Nov. 28, 2000, provisional application No. 60/244,504, filed on Oct. 31, 2000.

(51) Int. Cl.
*A23K 1/00* (2006.01)

(52) U.S. Cl.
USPC .................... 514/440; 426/635; 426/805

(58) Field of Classification Search
USPC ................................ 426/635, 805
See application file for complete search history.

(56) References Cited

U.S. PATENT DOCUMENTS

| | | | |
|---|---|---|---|
| 4,006,266 A * | 2/1977 | Bone et al. ................ 426/623 |
| 4,247,562 A | 1/1981 | Bernotavicz |
| 4,883,672 A | 11/1989 | Shug et al. |
| 5,006,361 A | 4/1991 | Cox |
| 5,030,458 A | 7/1991 | Shug et al. |
| 5,118,505 A | 6/1992 | Koltringer |
| 5,292,538 A | 3/1994 | Paul et al. |
| 5,339,771 A | 8/1994 | Axelrod |
| 5,419,283 A | 5/1995 | Leo |
| 5,569,670 A | 10/1996 | Weischer et al. |
| 5,599,835 A | 2/1997 | Fischer |
| 5,621,117 A | 4/1997 | Bethge |
| 5,728,735 A | 3/1998 | Ulrich et al. |
| 5,730,988 A | 3/1998 | Womack |
| 5,851,573 A | 12/1998 | Lepine et al. |
| 5,883,083 A | 3/1999 | Harless |
| 5,894,029 A * | 4/1999 | Brown et al. ................ 426/302 |
| 5,916,912 A | 6/1999 | Ames et al. |
| 5,937,790 A | 8/1999 | Ito et al. |
| 5,976,568 A | 11/1999 | Riley |
| 5,977,162 A | 11/1999 | Seidman |
| 5,981,767 A | 11/1999 | Tanner et al. |
| 6,080,788 A | 6/2000 | Sole et al. |
| 6,117,477 A | 9/2000 | Paluch |
| 6,190,591 B1 | 2/2001 | van Lengerich |
| 6,232,346 B1 | 5/2001 | Sole et al. |
| 6,335,361 B1 | 1/2002 | Hamilton |
| 6,365,211 B1 | 4/2002 | Corrigan |
| 6,379,727 B1 | 4/2002 | Addy |
| 6,426,362 B1 | 7/2002 | Miller et al. |
| 6,479,069 B1 | 11/2002 | Hamilton |
| 6,572,888 B2 | 6/2003 | Byrd |
| 6,669,975 B1 | 12/2003 | Abene et al. |
| 6,914,071 B2 | 7/2005 | Zicker et al. |
| 7,282,225 B1 | 10/2007 | Davis et al. |
| 2001/0028896 A1 | 10/2001 | Byrd |
| 2001/0043983 A1* | 11/2001 | Hamilton ................ 426/635 |
| 2001/0044448 A1 | 11/2001 | Dib |
| 2002/0006907 A1 | 1/2002 | Gardiner et al. |
| 2002/0076469 A1 | 6/2002 | Zicker et al. |
| 2002/0076470 A1 | 6/2002 | Zicker et al. |
| 2002/0115710 A1 | 8/2002 | Zicker et al. |
| 2002/0119182 A1 | 8/2002 | Zicker et al. |
| 2003/0035821 A1 | 2/2003 | Heaton et al. |
| 2003/0044466 A1 | 3/2003 | Markey et al. |
| 2003/0060503 A1 | 3/2003 | Hamilton |
| 2003/0224061 A1 | 12/2003 | Pacioretty et al. |
| 2004/0047896 A1 | 3/2004 | Malnoe et al. |
| 2004/0068010 A1 | 4/2004 | Zicker et al. |

(Continued)

FOREIGN PATENT DOCUMENTS

| | | |
|---|---|---|
| CA | 2285490 | 4/2001 |
| CA | 2427692 | 5/2002 |

(Continued)

OTHER PUBLICATIONS

Dictionary.com: Definition for "prevent" (printed Jul. 12, 2012).*
Petwave (Treatment & Prognosis of Renal Dysplasia in Dogs. Petwave.com (2012)).*
Samantha Coe (Osteoarthritis in Dogs. http://www.vetbase.co.uk/information/osteoarthritis-dogs.php, (2012)).*
Vancouver Vets. Aug 22, 2011. Osteoarthritis in dogs. Treatment & Prognosis. http://www.articlesbase.com/health-articles/osteoarthritis-in-dogs-treatment-prognosis-5146156.html.*
www.PetsOnThePark.com.au/prod207.htm. Accessed Dec. 17, 2007.*
Epinions.com (http://www.epinions.com/review/Hill_s_Science_Diet_Canine_Senior/pets-review-7CC1-752D32C-39779C59-prod4). Jul. 2000.*

(Continued)

*Primary Examiner* — Jeffrey S. Lundgren
*Assistant Examiner* — Chris Simmons
(74) *Attorney, Agent, or Firm* — Thomas M. Hunter

(57) ABSTRACT

The invention encompasses compositions and methods for treating or preventing disorders in companion animals, wherein the compositions and methods include feeding the companion animal a composition including lipoic acid or a salt thereof.

70 Claims, No Drawings

(56) References Cited

U.S. PATENT DOCUMENTS

| | | |
|---|---|---|
| 2004/0166157 A1 | 8/2004 | Thombre |
| 2005/0100617 A1 | 5/2005 | Malnoe et al. |
| 2005/0123628 A1 | 6/2005 | Zabrecky |
| 2005/0123643 A1 | 6/2005 | Cupp et al. |
| 2008/0317725 A1 | 12/2008 | Baum |
| 2009/0176864 A1 | 7/2009 | Zicker et al. |

FOREIGN PATENT DOCUMENTS

| | | |
|---|---|---|
| CA | 2427261 | 6/2002 |
| CN | 1323165 A | 11/2001 |
| CN | 1829448 A | 9/2006 |
| CN | 101106984 | 1/2008 |
| CN | 101107012 | 1/2008 |
| CN | 101119634 | 2/2008 |
| CN | 101128109 | 2/2008 |
| CN | 101132701 | 2/2008 |
| DE | 19818563 | 10/1999 |
| EP | 0427247 | 5/1991 |
| EP | 1118332 | 7/2001 |
| EP | 247456 | 10/2002 |
| EP | 1637041 | 3/2006 |
| EP | 1339292 | 12/2009 |
| JP | H2-49723 A | 2/1990 |
| JP | 10-042798 A | 2/1998 |
| JP | 2003-052338 A | 2/2003 |
| JP | 2003-261456 A | 9/2003 |
| JP | 2003-529347 | 10/2003 |
| JP | 2004-512053 | 4/2004 |
| JP | 2004-519241 | 7/2004 |
| JP | 2007-062326 | 3/2007 |
| JP | 2007-062332 | 3/2007 |
| JP | 2007308468 | 11/2007 |
| JP | 2008063234 | 3/2008 |
| JP | 2008280322 | 11/2008 |
| RU | 2071319 | 1/1997 |
| RU | 2099078 | 12/1997 |
| RU | 2303373 | 7/2007 |
| WO | 9402036 | 2/1994 |
| WO | WO 98/004361 | 2/1998 |
| WO | WO 98/041113 | 9/1998 |
| WO | 9804361 | 10/1998 |
| WO | WO 98/043617 | 10/1998 |
| WO | WO 98/057627 | 12/1998 |
| WO | WO 99/066913 | 12/1999 |
| WO | WO2000/02553 | 1/2000 |
| WO | WO 00/011968 | 3/2000 |
| WO | WO 00/030666 | 6/2000 |
| WO | WO 00/044375 | 8/2000 |
| WO | WO 00/048594 | 8/2000 |
| WO | WO 00/049891 | 8/2000 |
| WO | WO 01/17366 | 3/2001 |
| WO | WO 01/21208 | 3/2001 |
| WO | WO 01/58271 | 8/2001 |
| WO | WO 02/35943 | 5/2002 |
| WO | WO 02/45525 | 6/2002 |
| WO | WO 02/052955 | 7/2002 |
| WO | WO 02/071874 | 9/2002 |
| WO | WO 03/035056 | 5/2003 |
| WO | WO 2005/006877 | 1/2005 |
| WO | WO 2005/013714 | 2/2005 |
| WO | WO 2005/058064 | 6/2005 |
| WO | WO 2006/058248 | 6/2006 |
| WO | WO 2006/058278 | 6/2006 |
| WO | WO 2006/069241 | 6/2006 |
| WO | WO 2006/071919 | 7/2006 |
| WO | WO 2006/074089 | 7/2006 |
| WO | WO 2007/009111 | 1/2007 |
| WO | WO2007/022344 | 2/2007 |
| WO | WO2007/063095 | 6/2007 |
| WO | WO 2007/094669 | 8/2007 |
| WO | WO 2007/149815 | 12/2007 |
| WO | WO2008/151131 | 12/2008 |
| WO | WO 2010/083409 | 7/2010 |
| ZA | 9605149 A | 1/1997 |

OTHER PUBLICATIONS

Kim et al. Antioxidant alpha-lipoic acid inhibits osteoclast differentiation be reducing nuclear factor-kappaB DNA binding and prevents in vivo bone resorption induced by receptor activator of nuclear factor-kappaaB ligand and tumor necrosis factor-alpha Free Radical Biology and Medicine, Elsevier Science, US LKND-DIO:10.1016/J. Freeadbiomed.2005.10.066,vol. 40, No. 9, 1 May 2006, pp. 1483-1489.
Database WPI Week 200659 Thomson Scientific, London GB AN 2006-573787. XP002607399 &JP2006219467 A (Oriza YUKA KK) Aug. 24, 2006*abstract.
PCT Search Report dated Nov. 12, 2010.
Sastre et al., "A Ginkgo Biloba Extract (EGb 761) Prevents Mitochondrial Aging by Protecting Against Oxidative Stress," Free Radical Biology & Medicine, Jan. 15, 1998, pp. 298-304, vol. 24, Issue 2.
www.PetsOnThePark.com.au/prod207.htm.
Amazon.com: Hill's Science Diet Canine Senior (http://www.amazon.com/dp/B00063304U?smid=A2LDZGFAGG1QXE&tag-dealtime-pet-20&linkCode=asn.
Epinions.com (http://www.epinions.com/review/Hill_s_Science_Diet_Canine_Senior/pets-review-7CC1-752D32C-39779C59-prod4) (Jul. 2000).
David Dzanis (J Nutr. Dec. 1994; 124(12Suppl):2535S-2539S).
Anonymous, 2009, Dogs and Cats—Different Species, Different Needs, Retrieved from the internet http://www.felinefuture.com/?p=521, pp. 1-4.
AAFCO, 2003, Official Publication of the American Association of Feed Control Officials, p. 220.
AAFCO, 2004, American Association of Feed Control Officials Official Publication pp. 129-137.
Aksenova et al., 1999, "Oxidation of cytosolic proteins and expression of creatine kinase BB in frontal lobe in different neurodegenerative disorders," Dement. Geriatr. Cogn. Disord. 10(2):158-165.
Ames et al., 1993, "Oxidants, Antioxidants and the Degenerative Diseases of Aging," Proc. Natl. Acad. Sci. 90(17):7915-7922.
Ames, 1998, "Micronutrients Prevent Cancer and Delay Aging," Toxicol. Lett. 102-103:5-18.
Arivazhagan et al., 2000, "Antioxidant Lipoate and Tissue Antioxidants in Aged Rats," J. Nutr. Biochem. 11(3):122-127.
Arivazhagan et al., 2001, "Effect of DL-α-Lipoic Acid on the Status of Lipid Peroxidation and Antioxidants in Mitochondria of Aged Rats," J. Nutr. Biochem. 12:2-6.
Austad, 2008, "Advances in Vertebrate Aging Research 2007," Aging Cell 7(2):119-124.
Beckman et al., 1998, "Mitochondrial Aging: Open Questions," Annals NY Acad. Sci. 854:118-127.
Beckman et al., 1998, "The Free Radical Theory of Aging Matures," Physiol. Rev. 78(2):547-581.
Berkson, 1999, "A conservative triple antioxidant approach to the treatment of hepatitis C. Combination of alpha lipoic acid (thioctic acid), silymarin, and selenium: three case histories," Med. Klin 94(Suppl. 3):84-89 Medline AN: NLM10554539 Abstract.
Bezlepkin et al., 1996, "The prolongation of survival in mice by dietary antioxidants depends on their age by the start of feeding this diet," Mech. Ageing Dev. 92(2-3):227-234.
Bickford et al., 2000, "Antioxidant-rich diets improve cerebellar physiology and motor learning in aged rats," Brain Res. 866(1-2):211-217.
Blagosklonny, 2007, "An anti-aging drug today: from senescence-promoting genes to anti-aging pill," Drug Discovery Today 12(5/6):218-224.
Borras et al., 1999, "Age-related changes in the brain of the dog," Vet. Pathol. 36(3):202-211.
Branam, 1987, "Dietary Management of Geriatric Dogs and Cats," Vet. Tech. Vet. Learning Syst. 8(10):501-503.
Brigelius-Flohe et al., 1999, "Vitamin E: Function and Metabolism," FASEB J. 13:1145-1155.

(56) References Cited

OTHER PUBLICATIONS

Bruce-Keller et al., 1998, "4-Hydroxynonenal, a product of lipid peroxidation, damages cholinergic neurons and impairs visuospatial memory in rats," J. Neuropathol. And Exp. Neurol. 57(3):257-267.
Cantuti-Castelvetri et al., 2000, "Neurobehavioral Aspects of Antioxidants in Aging," Int. J. Develop. Neurosci. 18(4-5):367-381.
Cao et al., 1998, "Increases in Human Plasma Antioxidant Capacity after Consumption of Controlled Diets High in Fruit and Vegetables," Amer. J. Clin. Nutr. 68:1081-1087.
Caprioli et al., 1990, "Age-dependent deficits in radial maze performance in the rat: effect of chronic treatment with acetyl-L-carnitine," Prog. Neuro-Psychopharmacol. & Biol. Psychiat. 14(3):359-369.
Chandra, 2001, "Effect of vitamin and trace-element supplementation on cognitive function in elderly subjects," Nutrition 17(9):709-712.
Christen, 2000, "Oxidative stress and Alzheimer disease," Amer. J. Clin. Nutr. 71(2):621S-629S.
Cotman et al., 2002, "Brain Aging in the Canine: A Diet Enriched in Antioxidants Reduces Cognitive Dysfunction," Neurobiol. Of Aging 23(5):809-818.
Crayhon, 1998, "Real Power of Antioxidants," Total Health 20(2):27-35.
Cummings et al., 1996, "The Canine as an Animal Model of Human Aging and Dementia," Neurobiol. Of Aging 17:259-268.
Cutler, 1991, "Antioxidants and Aging," Amer. J. Clin. Nutr. 53(Suppl. 1):373S-379S.
Dodd et al., 2003, "Can a Fortified Food Affect Behavioral Manifestations of Age-Related Cognitive Decline in Dogs?" Veterinary Medicine 98:396-408.
Droge, 2003, "Oxidative stress and aging," Adv. Exp. Med. Biol. 543:191-200.
Dunn, 2009, "Cats Are Different," Retrieved from the internet http://www.catsofaustralia.com/cat-nutrition.htm, p. 104.
Emmons, 1999, "Antioxidants to the Rescue," South Bend Tribune pp. 1-4.
Ernst, 1999, "Diet and Dementia, Is There a Link? A Systemati Review," Nutr. Neurosci. 2:1-6.
Estrada et al., 2001, "The Effects of Diet and Age on the Performance of the Landmark Discrimination Learning Task," 31st Ann. Meeting of Soc. For Neurosci., San Diego, CA 27(1):279, Abstract Biosis AN: PREV200100472166.
Frei, 1999, "Molecular and Biological Mechanisms of Antioxidant Action," FASEB J. 13:963-964.
Fryer, 1998, "Vitamin E Status and Neurodegenerative Disease," Nutritional Neurosci. 1(5):327-351.
Fuchs et al., 1994, "Antioxidant inhibition of skin inflammation induced by reactive oxidants: evaluation of the redox couple dihydrolipoate/lipoate," Skin Pharmacol. 7(5):278-284.
Fujimoto et al., 1989, "The effect of dietary docosahexaenoate on the learning ability of rats," in: Health Effects of Fish and Fish Oils, Chandra, ed., ARTS Biomedical Publishers and Distributors, St. John's, Newfoundland, pp. 275-284.
Gabbita et al., 1998, "Increased nuclear DNA oxidation in the brain in Alzheimer's disease," J. Neurochem. 71(5):2034-2040.
Grundman, 2000, "Vitamin E and Alzheimer disease: the basis for additional clinical trials," Amer. J. Clin. Nutr. 71(2):6305-6365.
Hagen et al., 1999, "(R)-alpha-lipoic acid-supplemented old rats have improved mitochondrial function, decreased oxidative damage, and increased metabolic rate," FASEB J. 13(2):411-418.
Han et al., 1997, "Lipoic acid increases de novo synthesis of cellular glutathione by improving cystine utilization," BioFactors 6(3):321-338.
Harman, 1961, "Prolongation of the normal lifespan and inhibition of spontaneous cancer by antioxidants," J. Gerontol. 16:247-254.
Harman, 1993, "Free Radical Theory of Aging: A Hypothesis on Pathogenesis of Senile Dementia of the Alzheimer's Type," Age 16:23-30.
Hawthorne, 2002, "Nutritional Requirements of Aging Dogs and Cats," Waltham Focus 12(1):28-34.

Head et al., 1995, "Spatial Learning and Memory as a Function of Age in the Dog," Behavioral Neurosci. 109(5):851-858.
Head et al., 2002, "A Longitudinal Dietary Antioxidant Intervention in Aged Canines Improves Learning and Reduces Peripheral Measures of Oxidative Damage," 32nd Annual Meeting of Soc. For Neurosci., Orlando, FL Biosis AN: PREV200300381007.
Hill et al., 2004, "Lipoic acid is 10 times more toxic in cats than reported in humans, dogs or rats," J. Animal Physiol. A. Animal Nutrition 88(3-4):150-156.
Ikeda-Douglas et al., 2004, "Prior Experience, Antioxidants, and Mitochondrial Cofactors Improve Cognitive Function in Aged Beagles," Vet. Ther. 5(1):5-16.
Information Network Village, 2011, Specialties (Agricultural Produce) http://www.invil.org/english/specialty/vegetable/potato/contents.jsp?con_no=602519&page_no=1.
International Search Report and Written Opinion in International Application No. PCT/US01/048495, mailed Jul. 30, 2002.
International Search Report and Written Opinion in International Application No. PCT/US01/049654, mailed Jul. 30, 2002.
International Search Report and Written Opinion in International Application No. PCT/US05/047192, mailed Jun. 14, 2000.
International Search Report and Written Opinion in International Application No. PCT/US06/027615, mailed Nov. 22, 2006.
International Search Report and Written Opinion in International Application No. PCT/US09/058244, mailed Dec. 14, 2009.
International Search Report and Written Opinion in International Application No. PCT/US09/068166, mailed May 7, 2010.
International Search Report and Written Opinion in International Application No. PCT/US09/068244, mailed Feb. 18, 2010.
International Search Report and Written Opinion in International Application No. PCT/US09/069686, mailed Nov. 12, 2010.
International Search Report and Written Opinion in International Application No. PCT/US10/041888, mailed Nov. 12, 2010.
Jayachandran et al., 1996, "Status of lipids, lipid peroxidation, and antioxidant systems with Vitamin C supplementation during aging in rats," J. Nutritional Biochem. 7(5):270-275.
Jones et al., 1997, "Evidence for the involvement of docosahexaenoic acid in cholinergic stimulated signal transduction at the synapse," Neurochemical Research 22(6):663-670.
Joseph et al., 2000, "Oxidative stress protection and vulnerability in aging: putative nutritional implications for intervention," Mechanisms of Ageing and Development 116(2-3):141-153.
Joseph, 2009, "Nutrition, Brain Aging, and Neurodegeneration," J. Neurosci. 29(41):12795-12801.
Kalaiselvi et al., 1998, "Effect of L-Carnitine on the Status of Lipid Peroxidation and Antioxidants in Aging Rats," J. Nutr. Biochem. 9:575-581.
Kealy et al., 2002, "Effects of diet restriction on life span and age-related changes in dogs," J. Amer. Vet. Med. Assoc. 220(9):1315-1320.
Keller et al., 1999, "4-hydroxynonenal increases neuronal susceptibility to oxidative stress," J. Neurosci. Res. 58(6):823-830.
Kolb et al., 1997, "Zum Bedarf an Vitaminen und an Ascorbinsaure beim Hund, mit Bemerkungen zur Publikation von M. Torel, TU51, 785-790, 996," Tieraerztliche Umschau 52(12):728-733.
Lee et al., 2004, "The impact of alpha-lipoic acid, coenzyme Q10 and caloric restriction on life span and gene expression patterns in mice," Free Radical Biol. Med. 36(8):1043-1057.
Leveque, 1998, "Cognitive Dysfunction in Dogs, Cats an Alzheimer's-Like Disease," J. Amer. Vet. Med. Assoc. 212(9):1351.
Liu et al., 1999, "Stress, aging, and brain oxidative damage," Neurochem. Res. 24(11):1479-1497.
Lovell et al., 1998, "Elevated 4-Hydroxynonenal in Ventricular Fluid in Alzheimer's Disease," Neurobiol. Of Aging 18:457-461.
Lovell et al., 1999, "Increased DNA oxidation and decreased levels of repair products in Alzheimer's disease ventricular CSF," J. Neurochem. 72(2):771-776.
Markesbery et al., 1998, "Four-Hydroxnonenal, a Product of Lipid Peroxidation, Is Increased in the Brain in Alzheimer's Disease," Neurobiol. Of Aging 19:33-36.
Markesbery et al., 1999, "Oxidative alterations in Alzheimer's disease," Brain Pathol. 9(1):133 146.

(56) References Cited

OTHER PUBLICATIONS

McGahon et al., 1999, "Age-related changes in oxidative mechanisms and LTP are reversed by dietary manipulation," Neurobiology of Aging 20(6):643-653.
McGahon et al., 1999, "Age-related changes in LTP and antioxidant defenses are reversed by an alpha-lipoic acid-enriched diet," Neurobiology of Aging 20(6):655-664.
McGahon et al., 1999, "Age-related changes in synaptic function: analysis of the effect of dietary supplementation with omega-3 fatty acids," Neuroscience 94(1):305-314.
Melder, 1982, "Modulation of natural killer cell activity in mice after interferon induction: depression of activity and depression of in vitro enhancement by interferon," Infect. Immun. 36(3):990-995.
Milgram et al., 1994, "Cognitive Functions and Aging in the Dog: Acquisition of Nonspatial Visual Tasks," Behavioral Neurosci. 108(1):57-68.
Milgram et al., 1999, "Landmark Discrimination Learning in the Dog," Learning & Memory 6(1):54-61.
Milgram et al., 2000, "Landmark Discrimination Learning in Aged Dogs Is Improved by Treatment with an Antioxidant Enriched Diet," Poster Presentation No. 193.9 at Society for Neuroscience Meeting New Orleans, LA.
Milgram et al., 2001, "Age Dependent Cognitive Dysfunction in Canines: Dietary Intervention," Proc. of the Third International Conference on Veterinary Behavioural Medicine, Overall, ed., Universities Federation for Animal Welfare, publisher pp. 53-57.
Milgram et al., 2002, "Dietary Enrichment Counteracts Age-Associated Cognitive Dysfunction in Canines," Neurobiol. of Aging 23(5):737-745.
Milgram et al., 2002, "Landmark Discrimination Learning in the Dog: Effects of Age, an Antioxidant Fortified Food, and Cognitive Strategy," Neurosci. Biobehav. Rev. 26(6):679-695.
Milgram et al., 2004, "Long-Term Treatment with Antioxidants and a Program of Behavioral Enrichment Reduces Age-Dependent Impairment in Discrimination and Reversal Learning in Beagle Dogs," Exp. Gerontol. 39(5):753-765.
Milgram et al., 2005, "Learning Ability in Aged Beagle Dogs is Preserved by Behavioral Enrichment and Dietary Fortification: A Two-Year Longitudinal Study," Neurobiology of Aging 26(1):77-90.
Milgram et al., 2007, "Acetyl-L-carnitine and alpha-lipoic acid supplementation of aged beagle dogs improves learning in two landmark discrimination tests," FASEB J. 21(13):3756-3762.
Nourhashemi et al., 2000, "Alzheimer disease: protective factors," Amer. J. Clin. Nutr. 71(2):643S-649S.
Packer et al., 1995, "Alpha-Lipoic Acid as a biological antioxidant," Free Radical Biol. & Med. 19(2):227-250.
Packer et al., 1997, "Neuroprotection by the metabolic antioxidant alpha-lipoic acid," Free Radical Biol. & Med. 22(1-2):359-378.
Pastuszka et al., 2007, "Alpha-lipoic acid may be a clinically useful therapy in interstitial cystitis," Medical Hypotheses 69(4):957-958.
Patrick, 2000, "Nutrients and HIV: part three - N-acetylcysteine, alpha-lipoic acid, L-glutamine, and L-carnitine," Alt. Med. Review 5(4):290-305.
Perkins et al., 1999, "Association of antioxidants with memory in a multiethnic elderly sample using the Third National Health and Nutrition Examination Survey," Amer. J. Epidemiol. 150(1):37 44.
Podda et al., 1994, "Alpha-lipoic acid supplementation prevents symptoms of vitamin E deficiency," Biochem. Biophys. Res. Commun 204(1):98-104.
Pratico et al., 1998, "Increased F2-isoprostanes in Alzheimer's disease: evidence for enhanced lipid peroxidation in vivo," FASEB J. 12(15):1777-1783.
Pugh et al., eds., 2000, Stedman's Medical Dictionary, 27th Edition, Williams & Wilkins, p. 377.
Radak et al., 2001, "Regular exercise improves cognitive function and decreases oxidative damage in rat brain," Neurochem. International 38(1):17-23.

Riedel et al., 1998, "Nutrients, age and cognitive function," Curr. Opin. Nutr. Metab. Care 1(6):579-585.
Rogers, 2001, "A healthy body, a healthy mind: long-term impact of diet on mood and cognitive function," Proceedings of the Nutrition Society 60(1):135-143.
Rosenberg et al., 1959, "Effect of $\alpha$-lipoic acid on vitamin C and vitamin E deficiencies," Arch. Biochem. Biophys. 80(1):86-93.
Roy et al., 1998, "Redox regulation of cell functions by alpha-lipoate: biochemical and molecular aspects," BioFactors 7(3):263-267.
Roy et al., 1998, "Redox regulation of cell functions by alpha-lipoate: biochemical and molecular aspects," BioFactors 8(1-2):17-21.
Ruehl et al., 1998, "Canine Cognitive Dysfunction," Ch. 13 in: *Psychopharmacology of Animal Behavior Disorders*, Wiley-Blackwell, publisher, Dodman et al., eds., pp. 283-304.
Ruvo et al., 2000, "Nutritional antioxidants as antidegenerative agents," Int. J. Developmental Neurosci. 18(4-5):359-366.
Rybak et al., 1999, "Dose dependent protection by lipoic acid against cisplatin-induced ototoxicity in rats: antioxidant defense system," Toxicol. Sci. 47(2):195-202.
Sano et al., 1997, "A Controlled Trial of Selegiline, Alpha-Tocopherol, or Both as Treatment for Alzheimer's Disease. The Alzheimer's Disease Cooperative Study," New England J. Med. 336(17):1216-1222.
Savitha et al., 2005, "Oxidative stress on mitochondrial antioxidant defense system in the aging process: role of DL-alpha-lipoic acid and L-carnitine," Clinica Chimica Acta 355(1-2):173-180.
Schoenherr et al., 1997, "Nutritional modification of inflammatory diseases," Seminars in Veterinary Medicine and Surgery (Small Animal) 12(3):212-222.
Schupke et al., 2001, "New metabolic pathways of alpha-lipoic acid," Drug Metab. Dispos. 29(6):855-862.
Shigenaga et al., 1994, "Oxidative damage and mitochondrial decay in aging," PNAS 91(23):10771-10778.
Siwak et al., 2000, "Age-associated changes in non-cognitive behaviors in a canine model of aging," Soc. Neurosci. 26(2):2332, Abstract No. 873.3.
Siwak et al., 2005, "Chronic antioxidant and mitochondrial cofactor administration improves discrimination learning in aged but not young dogs," Progress in Neuro-Psychopharmacol. Biological Psychiatry 29(3):461-469.
Siwak et al., 2003, "Locomotor Activity Rhythms in Dogs Vary with Age and Cognitive Status," Behavioral Neurosci. 117(4):813-824.
Socci et al., 1995, "Chronic antioxidant treatment improves the cognitive performance of aged rats," Brain Research 693(1-2):88-94.
Stoll et al., 1993, "The potent free radical scavenger alpha-lipoic acid improves memory in aged mice: putative relationship to NMDA receptor deficits," Pharmacol. Biochem. & Behavior 46(4):799-805.
Stoll et al., 1994, "The potent free radical scavenger alpha-lipoic acid improves cognition in rodents," Ann. NY Acad. Sci. 717:122-128.
Syufy, 2007, "Q. How Long Is the Common Cat Supposed to Live?" http://cats.about.com/cs/catmanagement101/f/lifespan_cats.htm website retrieved Nov. 12, 2007.
Tapp et al., 2003, "An Antioxidant Enriched Diet Improves Concept Learning in Aged Dogs," 33rd Annual Meeting of Soc. For Neurosci., New Orleans, LA Biosis AN: PREV200400205135.
Tsokos et al., 1982, "Natural killer cells and interferon responses in patients with systemic lupus erythematosus," Clin. Exp. Immunol 50(2):239-245.
Vazour, 2012, "Dietary Polyphenols as Modulators of Brain Functions: Biological Actions and Molecular Mechanisms Underpinning Their Beneficial Effects," Oxidative Med. and Cell. Longevity vol. 2012, Article ID: 914273, 16 pp.
Villeponteau et al., 2000, "Nutraceutical interventions may delay aging and the age-related diseases," Exp. Gerontol. 35(9-10):1405-1417.
Weaver et al., 1988, "Health effects and metabolism of dietary eicosapentaenoic acid," Prog. Food Nutr. Sci. 12(2):111-150.
Youdim et al., 2000, "Essential fatty acids and the brain: possible health implications," Int. J. Devel. Neurosciences 18(4-5):383-399.

\* cited by examiner

COMPANION ANIMAL COMPOSITIONS INCLUDING LIPOIC ACID AND METHODS OF USE THEREOF

CROSS REFERENCE TO RELATED APPLICATIONS

This application is a continuation-in-part of pending application Ser. No. 11/154,210, filed Jun. 16, 2005, which is a continuation of application Ser. No. 09/978,132 filed Oct. 16, 2001, which issued as U.S. Pat. No. 6,914,071, which is a continuation-in-part of application Ser. No. 09/922,660 filed Aug. 6, 2001, which claims benefit of Provisional Application Ser. No. 60/253,448 filed Nov. 28, 2000 and Provisional Application Ser. No. 60/244,504, filed Oct. 31, 2000, each of which is incorporated herein by reference in its entirety.

FIELD OF THE INVENTION

The invention encompasses compositions and methods for treating or preventing disorders in companion animals, wherein the compositions and methods include feeding the companion animal a composition including lipoic acid or a salt thereof.

BACKGROUND OF THE INVENTION

Companion animals such as dogs and cats seem to suffer from aging problems. Some of these are manifested in commonplace sayings. One of these is "you can't teach an old dog new tricks." This saying arises from the observation that as dogs age, their mental capacity seems to diminish as well as physical abilities. Mental activities associated with thinking, learning and memory seem to be lessened (Cummings B J, Head E, Ruehl W, Milgram N W, Cotman C W 1996: The canine as an animal model of aging and dementia; Neurobiology of aging 17:259-268). Additionally, behavioural change can be manifested in the aging animals in association with the changing mental capacity. Many causes have been assigned to this lessening of capacity.

These losses in capacity are generally observed in aged canines and felines. Dogs of seven years or older and felines of seven years or older are considered aged and can experience this problem.

An important indicator of animal health is the body composition of the animal. An unhealthy diet and/or an unhealthy lifestyle can result in the animal having an unhealthy proportion of body fat, particularly in relation to lean muscle in the body. It is thought that a body fat amount in excess of 30% by weight indicates that the animal is unhealthy, particularly if the amount of body fat is in excess of 35% by weight.

The invention encompasses pet food compositions for companion animals, which have increased therapeutic and prophylactic efficacy over currently marketed companion food products.

SUMMARY OF THE INVENTION

The inventors have developed food compositions and methods of using the compositions for treating or preventing disorders in animals.

In accordance with the invention, there is a companion pet diet meeting ordinary nutritional requirements of an adult pet and further comprising a sufficient amount of an antioxidant or mixture thereof to inhibit the onset of deterioration of the mental capacity of said companion pet in its aged years.

Another embodiment encompasses a food composition for a companion animal, which includes lipoic acid or a salt thereof.

Another embodiment of the invention is a method for inhibiting the deterioration of the mental capacity of an aged companion pet, which comprises feeding said pet in his adult years an antioxidant or mixture thereof at sufficient levels to accomplish this inhibition.

In further accordance with the invention is a companion pet diet meeting ordinary nutritional requirements of an adult companion pet and further comprising an antioxidant selected from the group consisting of Vitamin E, Vitamin C, alpha-lipoic acid, l-carnitine and any mixtures thereof in quantities sufficient to inhibit the deterioration of the mental capacity of said pet in its aged years.

A still further embodiment of the invention is a method for increasing the mental capacity of an aged companion pet, which comprises feeding the pet in its adult years an amount of an antioxidant or mixture thereof sufficient to increase the mental capacity.

Another embodiment of the invention is a method for increasing the mental capacity of an adult companion pet, which comprises feeding the pet an amount of an antioxidant or mixture thereof sufficient to increase the mental capacity of said pet.

In all of these methods, it is desirable to administer the antioxidant or mixture thereof in the diet of the animal.

DETAILED DESCRIPTION OF THE INVENTION

General Description

The invention encompasses food compositions including an amount of lipoic acid or a salt thereof.

In certain embodiments, the effective amount is at least about 25 ppm.

In certain embodiments, the effective amount is at least about 50 ppm.

In certain embodiments, the effective amount is at least about 100 ppm.

In certain embodiments, the effective amount is about 100 ppm to about 600 ppm.

In certain embodiments, the effective amount is about 100 ppm to about 200 ppm.

In certain embodiments, the companion animal is a dog.

In certain embodiments, the companion animal is a cat.

In certain embodiments, the effective amount is effective to prevent or treat a degenerative joint condition in a companion animal.

In certain embodiments, the degenerative joint condition is osteoarthritis.

In certain embodiments, the degenerative joint condition is cartilage damage.

In certain embodiments, the effective amount is effective to prevent or treat kidney-related disorders in a companion animal.

In certain embodiments, the effective amount is effective to enhance palatability to a companion animal.

In certain embodiments, the effective amount is effective to maintain or promote a healthy body composition in a companion animal.

In certain embodiments, the effective amount is effective for inducing weight loss in a companion animal.

In certain embodiments, the effective amount is effective for inducing loss of body fat in a companion animal.

In certain embodiments, the effective amount is effective for increasing the percentage of lean muscle mass in a companion animal.

In certain embodiments, the composition further comprises a protein, fat, carbohydrate, fiber, and combinations thereof.

In certain embodiments, the composition is a dog food.

In certain embodiments, the composition is a cat food.

In certain embodiments, the composition is a food, a nutritional diet, a supplement, an animal treat, or a toy.

In certain embodiments, the composition is in the form of a moist food.

In certain embodiments, the composition is in the form of a dry food.

The term "companion animal" used in the present invention includes any non-human animal suitable for being kept as a pet by humans including a dog, a cat, and a rodent. The compositions of the invention are in certain embodiments for the treatment of cats and/or dogs.

The term "dog" includes those dogs, which are companion animals such as Canis familiaris, working dogs and the like. The term dog is synonymous with the term canine.

The term "cat" includes those cats, which are, companion animals known as domestic cats or house cats.

The term "rodent" includes, but is not limited to, hamsters, mice, rats, guinea pigs, gerbils, rabbits, hedge hogs, ferrets, chinchillas etc.

All percentages expressed herein are by weight of the composition on dry matter basis unless specifically stated otherwise.

Compositions of the Invention

One embodiment of the invention encompasses compositions for companion animals including an effective amount of lipoic acid to prevent or treat a degenerative joint condition in a companion animal.

As used herein, the terms "lipoic acid or a salt thereof" includes, but is not limited to, for example, alpha-lipoic acid, a racemic mixture of lipoic acids, a lipoate salt, ester, amide or derivative thereof, for example as described in U.S. Pat. No. 5,621,117. In various embodiments, the lipoic acid can be administered in a composition comprising a wet or dry food composition, which may be in the form of a moist food, dry food, supplement or treat.

The lipoic acid may be incorporated therein or on the surface of any food composition, such as, by spraying or precipitation thereon or may be added to the diet by way of snack, supplement, treat or in the liquid portion of the diet such as water or another fluid. The lipoic acid may be administered as a powder, solid or as a liquid including a gel. An important aspect is that the animal be provided an effective amount of the lipoic acid to provide a positive effect. Typically, the source of lipoic acid is present in the composition in an amount of up to an amount which remains non-toxic to the animal.

The quantity of alpha-lipoic acid can vary from at least about 25 ppm, about 50 ppm, about 100 ppm, about 200 ppm, about 300 ppm, about 500 ppm, about 700 ppm, about 900 ppm, about 1100 ppm, about 1200 ppm, about 1400 ppm, about 1600 ppm, about 1800 ppm, about 2000 ppm, about 2200 ppm, about 2400 ppm, about 2600 ppm, about 2800 ppm, about 3000 ppm, or about 3500 ppm. In various embodiments, the range of lipoic acid that can be administered dogs is about 150 ppm to about 4500 ppm. In various embodiments, the range of lipoic acid that can be administered cats is about 65 ppm to about 2600 ppm. In certain illustrative embodiments, quantities can vary from about 100 ppm to an amount which remains non-toxic to the pet. In other embodiments, a range is from about 100 ppm to about 200 ppm.

In various embodiments, a food composition comprising lipoic acid provides a substantially nutritionally complete diet for the intended recipient animal. A "nutritionally complete diet" is a diet that includes sufficient nutrients for maintenance of normal health of a healthy animal on the diet.

The compositions of the invention include lipoic acid or salt thereof in an amount effective to treat or prevent a degenerative joint condition.

The lipoic acid or salt thereof is present at a concentration that is not deleterious to the intended animal's health. Thus, for example, the lipoic acid or salt thereof is present at a concentration that does not cause undesirable or toxic effects.

The invention is based upon the novel discovery that adding lipoic acid or salt thereof to a composition for consumption by a companion animal enhances palatability of the composition and increases the likelihood that an animal will consume the composition. Adding lipoic acid or salt thereof to a composition for consumption also increases the ingestion frequency and ingestion rate of the composition.

The composition can be a liquid or a solid food. When the composition is a liquid, the lipoic acid or salt thereof can be admixed with other components. Where the composition is solid, the lipoic acid may be coated on the composition, incorporated into the composition, or both.

In various embodiments, the lipoic acid or salt thereof may be added to the animal's food. In various embodiments, the lipoic acid or salt thereof may be added to the animal's food by a compounder or manufacturer at a site or by an animal's caregiver prior to feeding the animal. In various embodiments, the lipoic acid or salt thereof may be added during the processing of an animal's food, such as during and/or after mixing of other components of the composition that is then packaged and made available to consumers. Such processing may include extrusion, canning, baking, and the like or any other method or process of producing pet foods that is known in the art. In various embodiments, the lipoic acid or salt thereof may be contributed by a natural source like an animal or plant component, or the lipoic acid or salt thereof may be contributed by a synthetically derived source, or the lipoic acid or salt thereof may be contributed by a mixture of natural and synthetic sources.

The compositions in addition to lipoic acid or a salt thereof include at least one component suitable for consumption by a companion animal including, but not limited to, fats, carbohydrates, proteins, fibers, nutritional balancing agents such as vitamins, minerals, and trace elements, and mixtures thereof. One of ordinary skill in the art can select the amount and type of food ingredients for a typical food based upon the dietary requirements of the animal, for example, the animal's species, age, size, weight, health, and function.

The food ingredient part of the food composition can include up to about 100% of any particular food ingredient or can include a mixture of food ingredients in various proportions. In certain embodiments, the food composition includes a combination of food ingredients in amounts of about 0 wt. % to about 50 wt. % fat, about 0 wt. % to about 75 wt. % carbohydrate, about 0 wt. % to about 95 wt. % protein, about 0 wt. % to about 40 wt. % dietary fiber, and about 0 wt. % to about 15 wt. % of one or more nutritional balancing agents.

In certain embodiments, the fat and carbohydrate food ingredient is obtained from a variety of sources such as animal fat, fish oil, vegetable oil, meat, meat by-products, grains, other animal or plant sources, and mixtures thereof. Grains include wheat, corn, barley, and rice.

In certain embodiments, the protein food ingredient is obtained from a variety sources such as plants, animals, or both. Animal protein includes meat, meat by-products, dairy, and eggs. Meats include the flesh from poultry, fish, and animals such as cattle, swine, sheep, goats, and the like, meat by-products include lungs, kidneys, brain, livers, stomachs, and intestines. The protein food ingredient may also be free amino acids and/or peptides. Preferably, the protein food ingredient includes meat, a meat by-product, dairy products, or eggs.

In certain embodiments, the fiber food ingredient is obtained from a variety of sources such as vegetable fiber sources, for example, cellulose, beet pulp, peanut hulls, and soy fiber.

In certain embodiments, the nutritional balancing agents are obtained from a variety of sources known to skilled artisans, for example, vitamin and mineral supplements and food ingredients. Vitamins and minerals can be included in amounts required to avoid deficiency and maintain health. These amounts are readily available in the art. The National Research Council (NRC) provides recommended amounts of such nutrients for farm animals. See, e.g., Nutrient Requirements of Swine (10th Rev. Ed., Nat'l Academy Press, Wash. D.C., 1998), Nutrient Requirements of Poultry (9th Rev. Ed., Nat'l Academy Press, Wash. D.C., 1994), Nutrient Requirements of Horses (5th Rev. Ed., Nat'l Academy Press, Wash. D.C., 1989). The American Feed Control Officials (AAFCO) provides recommended amounts of such nutrients for dogs and cats. See American Feed Control Officials, Inc., Official publication, pp. 129-137 (2004). Vitamins generally useful as food additives include vitamin A, vitamin B1, vitamin B2, vitamin B6, vitamin B12, vitamin D, biotin, vitamin K, folic acid, inositol, niacin, and pantothenic acid. Minerals and trace elements useful as food additives include calcium, phosphorus, sodium, potassium, magnesium, copper, zinc, chloride, iron, selenium, iodine, and iron.

In certain embodiments, the food compositions may contain additional ingredients such as vitamins, minerals, fillers, palatability enhancers, binding agents, flavors, stabilizers, emulsifiers, sweeteners, colorants, buffers, salts, coatings, and the like known to skilled artisans. Stabilizers include substances that tend to increase the shelf life of the composition such as preservatives, synergists and sequestrants, packaging gases, stabilizers, emulsifiers, thickeners, gelling agents, and humectants. Examples of emulsifiers and/or thickening agents include gelatin, cellulose ethers, starch, starch esters, starch ethers, and modified starches. Specific amounts for each composition component, food ingredient, and other ingredients will depend on a variety of factors such as the particular components and ingredients included in the composition; the species of animal; the animal's age, body weight, general health, sex, and diet; the animal's consumption rate; the type of disease or condition being treated; and the like. Therefore, the component and ingredient amounts may vary widely and may deviate from the preferred proportions described herein.

In one illustrative embodiment, the composition may, for example, in addition to lipoic acid or a salt thereof also include at least one of the following:
 (a) about 0% to about 75% carbohydrate,
 (b) about 2% to about 50% fat,
 (c) about 0% to about 40% dietary fiber, and
 (d) about 0% to about 15% of one or more nutritional balancing agents.

The diet fed to the adult companion pet, for example, canine and feline is the standard normal diet fed to an animal of that age. Below is a typical diet for a canine of 1 to 6 years of age.

TABLE 1

Illustrative Companion Animal Pet Food Composition

| Ingredient | Target |
|---|---|
| Protein (% of dry matter) | 23 |
| Fat (% of dry matter) | 15 |
| Phosphorous (% of dry matter) | 0.6 |
| Sodium (% of dry matter) | 0.3 |

The compositions can contain additional ingredients intended to maintain or improve the health of the animal, for example, supplements, medications, herbs, holistic drugs and compositions, and the like.

The composition of the invention may include one or more additional ingredients to prevent or treat one or more diseases or conditions.

The component in the diet, which accomplishes this, is an antioxidant or mixture thereof. An antioxidant is a material that quenches a free radical. Examples of such materials include foods such as *Ginkgo Biloba*, citrus pulp, grape pomace, tomato pomace, carrot and spinach, all preferably dried as well as various other materials such as beta-carotene, selenium, coenzyme Q10 (ubiquinone), lutein, tocotrienols, soy isoflavones, S-adenosylmethionine, glutathione, taurine, N-acetylcysteine, Vitamin E, Vitamin C, alpha-lipoic acid, 1-carnitine and the like. Vitamin E can be administered as a tocopherol or a mixture of tocopherols and various derivatives thereof such as esters like vitamin E acetate, succinate, palmitate, and the like. The alpha form is preferable but beta, gamma and delta forms can be included. The d form is preferable but racemic mixtures are acceptable. The forms and derivatives will function in a Vitamin E like activity after ingestion by the pet. Vitamin C can be administered in this diet as ascorbic acid and its various derivatives thereof such as calcium phosphate salts, cholesteryl salt, 2-monophosphate, and the like which will function in a vitamin C like activity after ingesting by the pet. They can be in any form such as liquid, semisolid, solid and heat stable form. Alpha-lipoic acid can be administered into the diet as alpha lipoic acid or as a lipoate derivative as in U.S. Pat. No. 5,621,117, racemic mixtures, salts, esters or amides thereof. L-carnitine can be administered in the diet and various derivatives of carnitine such as the salts such as the hydrochloride, fumarate and succinates, as well as acetylated carnitine, and the like can be used.

The quantities administered in the diet, all as wt % (dry matter basis) of the diet, are calculated as the active material, per se, that is measured as free material. The maximum amounts employed should not bring about toxicity. At least about 100 ppm or at least about 150 ppm of Vitamin E can be used. A preferred range of about 500 to about 1,000 ppm can be employed. Although not necessary, a maximum of about 2000 ppm or about 1500 ppm is generally not exceeded. With respect to Vitamin C at least about 50 ppm is used, desirably at least about 75 ppm and more desirably at least about 100 ppm. A non-toxic maximum can be employed. The quantity of alpha-lipoic acid can vary from at least about 25, desirably at least about 50 ppm, more desirably about 100 ppm. Maximum quantities can vary from about 100 ppm to an amount which remains non-toxic to the pet. A preferred range is from about 100 ppm to about 200 ppm. For 1-carnitine about 50 ppm, desirably about 200 ppm, more desirably about 300 ppm for canines are a useful minimum. For felines, slightly higher minimums of l-carnitine can be employed such as about 100 ppm, 200 ppm, and 500 ppm. A non-toxic maximum quantity can be employed, for example, less than about 5,000 ppm. For canines, lower quantities can be employed, for example, less than about 5,000 ppm. For canines, a preferred range is about 200 ppm to about 400 ppm. For felines, a preferred range is about 400 ppm to about 600 ppm. Beta-carotene at about 1-15 ppm can be employed. Selenium at about 0.1 up to about 5 ppm can be employed. Lutein at least about 5 ppm can be employed. Tocotrienols at least about 25 ppm can be employed. Coenzyme Q10 at least about 25 ppm can be employed. S-adenosylmethionine at least about 50 ppm can be employed. Taurine at least about 1000 ppm can be employed. Soy isoflavones at least about 25 ppm can be used. N-acetylcysteine at least about 50 ppm can be used. Glutathione at least about 50 ppm can be used. *Gingko Biloba* at least 50 ppm of extract can be used.

The following are raw ingredients that are high in ORAC (Oxygen radical absorbing capacity) content: Spinach pomace, Tomato pomace, Citrus Pulp, Grape Pomace, Carrot granules, Broccoli, Green tea, *Ginkgo Biloba* and Corn gluten meal.

When added to the diet as 1% inclusions (for a total of 5% substitution for a low ORAC ingredient such as corn) they increased the ORAC content of the overall diet and increased the ORAC content of the plasma of the animals which ate the diet containing these components. Preferably, any ingredient with an ORAC content>25 μmole of Trolox equivalents per gram of dry matter could be used if added at 1% combination with four other 1% ingredients for a total of 5% addition to the diet. In certain embodiments, the compositions further include an effective amount of at least one substance selected from the group consisting of glucosamine, chondroitin, chondroitin sulfate, methylsulfonylmethane ("MSM"), creatine, antioxidants, *Perna canaliculata*, omega-3 fatty acids, omega-6 fatty acids and mixtures thereof.

In various embodiments, a supplement including an effective amount of lipoic acid or a salt thereof further includes an effective amount of at least one substance including aspirin, anti-inflammatories such as ibuprofen, COX-2 inhibitors, and other medicinal and pharmaceutical compositions and combinations thereof. Supplements include, but are not limited to, a feed used with another feed to improve the nutritive balance or performance of the total. Supplements include compositions that are fed undiluted as a supplement to other feeds, offered free choice with other parts of an animal's ration that are separately available, or diluted and mixed with an animal's regular feed to produce a complete feed. The AAFCO, for example, provides a discussion relating to supplements in the American Feed Control Officials, Inc. Official Publication, p. 220 (2003). Supplements may be in various forms including, for example, powders, liquids, syrups, pills, and encapsulated compositions.

In certain embodiments, the composition can be a treat. Treats include compositions that are given to an animal to entice the animal to eat during a non-meal time, for example, dog bones for canines. Treats may be nutritional wherein the composition includes one or more nutrients and may have a food-like composition. Non-nutritional treats encompass any other treats that are non-toxic. The composition or components are coated onto the treat, incorporated into the treat, or both. Treats of the invention can be prepared by an extrusion or baking process similar to those used for dry food. Other processes also may be used to either coat the composition on the exterior of existing treat forms or inject the composition into an existing treat form.

In certain embodiments, the composition can be a toy. Toys include chewable toys such as artificial bones. The lipoic acid or a salt thereof can form a coating on the surface of the toy or on the surface of a component of the toy, be incorporated partially or fully throughout the toy, or both. In one embodiment, the lipoic acid or a salt thereof is orally accessible by the intended user. There are a wide range of suitable toys currently marketed, for example, U.S. Pat. No. 5,339,771, U.S. Pat. No. 5,419,283, and references disclosed therein. This invention provides both partially consumable toys, for example, toys including plastic components, and fully consumable toys, for example, rawhides and various artificial bones. The invention preferably provides toys for use by a dog or a cat.

Preparation of the Compositions of the Invention

The compositions of the invention may be prepared in a canned or wet form using conventional food preparation processes known to skilled artisans. Typically, ground animal proteinaceous tissues are mixed with the other ingredients such as fish oils, cereal grains, balancing ingredients, special purpose additives (e.g., vitamin and mineral mixtures, inorganic salts, cellulose and beet pulp, bulking agents, and the like) and water in amounts sufficient for processing. These ingredients are mixed in a vessel suitable for heating while blending the components. Heating of the mixture is effected using any suitable manner, for example, direct steam injection or using a vessel fitted with a heat exchanger. Following the addition of the last ingredient, the mixture is heated to a temperature of about 50° F. to about 212° F. Temperatures outside this range are acceptable but may be commercially impractical without use of other processing aids. When heated to the appropriate temperature, the material will typically be in the form of a thick liquid. The thick liquid is filled into cans. A lid is applied, and the container is hermetically sealed. The sealed can is then placed into conventional equipment designed to sterilize the contents. Sterilization is usually accomplished by heating to temperatures of greater than about 230° F. for an appropriate time depending on the temperature used, the composition, and similar factors. The compositions of the present invention can be added to the food compositions before, during, or after preparation.

Food compositions may be prepared in a dry form using conventional processes known to skilled artisans. Typically, dry ingredients such as animal protein, plant protein, grains, and the like are ground and mixed together. Moist or liquid ingredients, including fats, oils, animal protein, water, and the like are then added to and mixed with the dry mix. The mixture is then processed into kibbles or similar dry pieces. Kibble is often formed using an extrusion process in which the mixture of dry and wet ingredients is subjected to mechanical work at a high pressure and temperature and forced through small openings and cut off into kibble by a rotating knife. The wet kibble is then dried and optionally coated with one or more topical coatings such as flavours, fats, oils, powders, and the like. Kibble also can be made from the dough using a baking process, rather than extrusion, wherein the dough is placed into a mold before dry-heat processing. The food compositions can be in the form of a treat using an extrusion or baking process similar to those described above for dry food or a toy such as those disclosed in U.S. Pat. Nos. 5,339,771 and 5,419,283. The compositions of the present invention can be added to the food compositions before, during, or after preparation.

Methods of Treating or Preventing Disorders with Compositions of the Invention

The invention also encompasses methods of treating or preventing certain disorders by administering a therapeutically or prophylactically effective amount of a composition including lipoic acid or a salt thereof to a companion animal in need thereof.

Adding significant quantities of an antioxidant or mixture thereof to the companion adult pet diet can bring about delay of the onset of demonstrative changes in the behaviour, particularly the deterioration of mental capacity, as specifically shown by problem-solving capacity, in an aged pet. The term, adult, is intended to mean, in general, a canine of at least 1 to 6 years and a feline of at least 1 to 6 years. An aged dog or cat is 7 years and above.

The loss of mental capacity for canines and felines has been observed for a number of years. This loss of mental capacity is manifested in numerous ways. For a canine, for example, it can be manifested as disorientation, house soiling, altered sleep-wake patterns, decreased or altered interaction with humans and other pets, and inability to learn and concentrate. These conditions can be manifested in felines as well. Alzheimer's, as exhibited in man, is not found in canines and felines.

Many theories have been advanced for this loss in mental capacity. To date, the inventors are unaware of any dietary course of action, which inhibits this loss of mental capacity or can actually bring about a positive change in mental capacity as measured by an objective parameter in dogs and cats.

The inventors have succeeded in accomplishing delaying the onset of this deterioration. By using the diet of their invention in adult companion pets it can be shown that aged pets mental capacity can be maintained for a longer period of time. Essentially the deterioration of mental capacity can be stopped or delayed. Memory and learning ability can be improved. Overall, mental alertness can be enhanced. Age related cognitive decline could be slowed. With respect to Cognitive Dysfunction Syndrome, its progress can be slowed in aged dogs and clinical signs associated with this Syndrome can be controlled. Prophylaxes where appropriate and pets in need of these components are the target group.

The invention is not limited to the particular methodology, protocols, and reagents described herein because they may vary. Further, the terminology used herein is for the purpose of describing particular embodiments only and is not intended to limit the scope of the present invention. As used herein and in the appended claims, the singular forms "a," "an," and "the" include plural reference unless the context clearly dictates otherwise. Similarly, the words "include", "includes", and "including" are to be interpreted inclusively rather than exclusively. Unless defined otherwise, all technical and scientific terms and any acronyms used herein have the same meanings as commonly understood by one of ordinary skill in the art in the field of the invention. Although any compositions, methods, articles of manufacture, or other means or materials similar or equivalent to those described herein can be used in the practice of the present invention, the preferred compositions, methods, articles of manufacture, or other means or materials are described herein.

All patents, patent applications, publications, and other references cited or referred to herein are incorporated herein by reference to the extent allowed by law. The discussion of those references is intended merely to summarize the assertions made therein. No admission is made that any such patents, patent applications, publications or references, or any portion thereof, is relevant prior art for the present invention and the right to challenge the accuracy and pertinence of such patents, patent applications, publications, and other references is specifically reserved.

EXAMPLES

This invention can be further illustrated by the following examples of preferred embodiments thereof, although it will be understood that these examples are included merely for purposes of illustration and are not intended to limit the scope of the invention unless otherwise specifically indicated.

Example 1

Seventeen adult beagle dogs 2-4 years of age (control n=8, antioxidant-enriched n=9) were randomly placed into a control or enriched diet group. The control diet contained 59 ppm Vitamin E and <32 ppm Vitamin C. The test diet had 900 ppm Vitamin E and 121 ppm Vitamin C, 260 ppm l-carnitine and 135 ppm alpha lipoic acid. Approximately 1 month after starting the diet, the first problem-solving task given to dogs was a landmark discrimination learning task, which is a test of spatial attention (Milgram et al., 1999 Milgram, N. W., Adams, B., Callahan, H., Head, E., Mackay, B., Thirlwell, C., & Cotman (1999), C. W. Landmark Discrimination Learning in the Dog. Learning & Memory, 6:54-61).

Landmark discrimination earning requires subjects to select a particular object based on proximity to an object. The initial learning, however, is based on the dogs' ability to earn an object discrimination task. We have previously found that the effects of age on discrimination learning depend on task difficulty.

The adult dogs on the enriched diet made fewer errors than the adult dogs on the control food when learning the landmark 0 test (control mean=31.1, enriched mean=15.1). The adult dogs proceeded on to landmark 1 and 2 testing, where the landmark is moved further away from the positive well. Adult dogs on enriched diet learned landmark 0-2 with less errors than those on the control (number of mean errors landmark 0+1+2 control=132.9; number of mean errors of dogs on enriched diet landmark 0+1+2=87.1).

Example 2

Thirty (30) adult, random source, dogs were utilized for this study. Dogs were at least 10 months of age, not pregnant, not lactating and of reasonable body weight prior to start of test. Animals were randomized into 5 groups for dietary treatment with 3 males and 3 females per each group.

All dogs were fed a control food (0 ppm dl-alpha-lipoic acid added) that met or exceeded all recommendations for nutrients as proposed by the American Association of Feed Control Officials (AAFCO 2000) during a 2 week prefeeding period (Table 2). Following the prefeeding period dogs were randomized into 5 treatment groups with one of the following dl-alpha lipoic acid target-inclusions (dry matter basis): 0 ppm, 150 ppm, 1500 ppm, 3000 ppm, 4500 ppm. In all diets, control and alpha lipoic acid, Vitamin E was added and was present at a level of 600-1000 International Units and Vitamin C was added at levels of 100-200 ppm.

Test foods were the sole source of nutrients except for water. Fresh water was provided ad libitum. After dogs were selected and initial body weights taken, a food dose was calculated for each dog based on the expected ME of the food. Initial food dose calculations were based on the maintenance energy requirement (MER) for the dog modified by a factor to account for normal activity as calculated by the following formula:

$$MER(kcal/day) = 1.6 \times RER(\text{Resting Energy Requirement})$$

where:

$$RER(kcal/day) = 70 \times \text{body weight}(kg)0.75$$

Dogs were weighed weekly and had food doses adjusted as needed in order to feed enough food to maintain their optimal body weight. Optimal body weight was determined to be 3 on a 5 point scale. If a dog did not maintain body weight within −10% of initial body weight, after adjustment of food dose, it was removed from the study. All measures of body weight and food intake were recorded.

Samples were ground and 0.100+/−0.001 g of sample was extracted twice into 5.0 mL phosphate buffer (10 mM $Na_2HPO_4$, 2 mM ethylenediaminetetraacetatic acid (EDTA), 0.9% NaCl, pH 7.4). 250 µL of extract was placed into a 5 mL glass centrifuge tube with a Teflon lined cap. 15 µL EDTA solution (100 mM EDTA, adjusted to pH 7.8 with about 1M NaOH) and 50 µL freshly prepared 5 mM dithioerythritol (DTE) were added. The solutions were vortexed and incubated at room temperature for 5 minutes. Then 10 μL of 1M $H_3PO_4$ and 2.0 mL diethyl ether were added. The tubes were capped, vortexed, and centrifuged at 1500×g for 3 minutes at room temperature. The ether layer was transferred to a separate 5 mL glass centrifuge tube, while the aqueous layer was extracted twice more with 1.5 mL ether. All extractions from the same sample were combined. The extracts are then dried in a nitrogen evaporator in a water bath at room temperature. At this point, the samples were capped and frozen overnight.

The dried extracts were then thawed and reconstituted with 70 μL SDS/EDTA solution (0.11% sodium dodecyl sulfate (SDS), 15 mM EDTA, 0.9% NaCl) and 5 μL freshly prepared 1 mM DTE. 50 μL of freshly prepared $NaBH_4$ was then added to each tube. The tubes were vortexed and incubated at room temperature for 10 minutes. After 10 minutes, the samples were frozen at −70° C. Before the solutions were thawed, 20 μL 2M HCl was added. After the solutions were thawed, 800 μL 100 mM $NH_4HCO_3$ was added. The solutions are vortexed and 5 μL of 100 mM monobromodiamane in acetonitrile solution (mBBr) was added. The solutions were then incubated in the dark for 90 minutes at room temperature.

Excess mBBr and the DTE derivative were removed from the samples after incubation by extraction with 1.5 mL dichloromethane. The aqueous layer was placed on the HPLC. The lipoic acid was separated using a mobile phase that consisted of 30% acetonitrile, 1% acetic acid, adjusted to pH 3.95 with about 2M $NH_4OH$ and was pumped at a flow rate of 1.0 mL/min with an isocratic elution for 15 minutes per injection. This preparation assumes that the density of the extruded food is equal to 1 g/mL.

Blood was collected aseptically for complete blood count, and blood biochemistry analysis 2 weeks prior to start and again at 0, 28, 56, 84, 112, 140 and 168 days of the study. In addition, 15 ml of whole blood was collected for isolation of lymphocytes at day 0, 28 and 84 of the dietary intervention.

Heparinized whole blood was layered onto a 50 ml Accuspin conical centrifuge tube (Sigma Chemical) and an equal volume of Phosphate buffered saline (PBS) was added. Samples were centrifuged at 700 g for 30 minutes without brake. The monocyte layer was harvested, transferred to a 15 ml conical centrifuge tube, resuspended in 1-3 ml of PB, and centrifuged as before (First wash). A second wash was performed as the first wash. Finally, cells were harvested and suspended in perchloric acid (10% w/v) and frozen at −70° C. until analysis.

Samples were transferred from −70° C. freezer into a cooler with dry ice in it. Vials were centrifuged at 12,000 rpm for 5 minutes in a refrigerated centrifuge. An aliquot of supernatant for glutathione (GSH) analysis was transferred to a conical test tube.

Derivatization of the acid soluble extracts was by the method of Reed and coworkers (Fariss et al) as modified by Jones (Jones et al)

Briefly, 150 μL extract or external standards were added into a 1.5 ml Eppendorf tube followed by addition of 20 μγ-Glu-Glu internal standard and 50 μL IAA added followed by mixing. The solution was adjusted to pH about 10 (purple color) by using KOH—$KHCO_3$ working solution. Solutions were incubated 1 hr. under room temperature in the dark. Sanger's reagent was added at the same volume as of the total volume and the solution was incubated overnight (20 hrs) in the dark at room temperature.

After incubation, the solution was centrifuged at 12000 rpm for 5 minutes with the supernatant transferred into another 1.5 ml eppendorf tube. 200 μL supernatant was added into an amber autovial, which had a 300 μL inlet, fix the top with a crimper for HPLC analysis.

Solvents and separation conditions were as described (Fariss, Jones). Levels of GSH and GSSG were quantified relative to authentic standards. Gamma-glutamyl-glutamate was used as an internal standard to assess derivatization efficiency.

Comparison of values for clinical chemistry, hematology and body weights vs baseline were analyzed by way of paired t-test on SAS for windows with significance set at $P<0.05$. Means of values at each measured time point were separated by a one-way ANOVA with significance set at $P<0.05$. The difference in GSH:GSSG between day 84 and baseline were analyzed between groups by way of SAS for windows in a one-way ANOVA with significance set at $P<0.05$.

Results

Concentrations of lipoic acid (ppm) in food as determined over 7 successive assays (0, 28, 56, 84, 112, 140, 168 days) were within the range of expected assay sensitivity and production parameters typically encountered at our facility (Table 2).

The food intake data were unremarkable. Most animals in all groups ingested more food at 6 months, on average, than at the beginning of the study. Body weight data were unremarkable except that some weight loss occurred initially in the 4500 ppm inclusion group but that change appeared to reverse by 6 months time. Body condition scores did not appear to be affected by this minor loss of weight.

The routine physical examinations did not reveal any evidence of nutrition related abnormalities or dl-alpha-lipoic acid toxicity. All animals in the study population remained normal during the entire course of the study. Occasional vomiting was observed in several animals during the course of the study; however, a trend was not observed that would lead one to the conclusion that the vomiting may be attributable to lipoic acid. One animal, in the highest inclusion group, was dropped from the study at day 21 for weight loss and leukocytosis. The leukocytosis in this animal had not resolved by the end of the study and is suspected to be attributable to some other disease process.

When serum biochemistry values for days 28, 56, 84, 112, 140, and 168 were compared with the initial values for the same group of dogs, several statistical differences were noted, however, none of these were considered biologically significant because these values were within or very near the laboratory reference range and consistent trends over months were noted. Comparisons between the controls and the other treatment groups at each time period also revealed several statistical differences, however, none of these were considered biologically significant because these values were within or very near the clinical laboratory reference ranges and no trends were present.

When the hematology values for days 28, 56, 84, 112, 140 and 168 were compared with the initial values for the same group of dogs, several statistical differences were noted; however, none of these were considered biologically significant because these values were within or very near the laboratory reference range and not trends were present. Comparison between the controls and the other treatment groups at each time period revealed several statistical differences; however, none of these were considered biologically significant because these values were within or very near the clinical laboratory reference ranges and no trends were present.

GSH:GSSG Ratio

The change in GSH:GSSG ratio over 84 days of feeding displayed a significant overall effect of diet ($P=0.024$) with all supplemented groups having an increase in the ratio (Table 3). ANOVA revealed a significant difference, compared to the basal food, for the lowest and highest inclusions, however, the largest numerical increase was in the lowest inclusion level. That is to say, the changes in the GSH:GSSG ratios for the highest and lowest inclusion were significantly different from the change observed over this same time period in the basal food. Ratios for 4 points could not be determined at day 84 as no GSSG was detectable in any of these samples (1 control, 3 treatment groups). As such, the values for supplemented groups may have displayed even higher ratios of GSH:GSSG if the assay had been sensitive enough to detect the low levels of GSSG at day 84.

TABLE 2

| Inclusion Rate Standard Percent (ppm) | Average | Standard Deviation | Target |
|---|---|---|---|
| 0 ppm | 24 ppm | 17 | N/A |
| 150 ppm | 151 ppm | 13 | 101 |
| 1,500 ppm | 1471 ppm | 113 | 98 |
| 3,000 ppm | 2869 ppm | 250 | 96 |
| 4,500 ppm | 4176 ppm | 642 | 93 |

TABLE 3

Change In Mean Ratio Of GSH:GSSG From Day 0 To Day 84 In Dogs Consuming DL-Alpha Lipoic Acid In An Extruded Food

| Inclusion | Difference in GSH:GSSG ratio - day 0 to day 84 Inclusion compared to baseline food | N | P value |
|---|---|---|---|
| 0 ppm | −9.2 +/− 26 | 5* | NA |
| 150 ppm | 70 +/− 20 | 6 | 0.003 |
| 1,500 ppm | 24 +/− 7 | 6 | 0.16 |
| 3,000 ppm | 10 +/− 4 | 4* | 0.46 |
| 4,500 ppm | 50 +/− 36 | 4* | 0.03 |

*1 dog in the control and 4,500 ppm group had no detectable GSSG at day 84 while 2 dogs in the 3,000 ppm group had no detectable GSSG at day 84.

Further observations with respect to alpha-lipoic acid are applicable. Chronic feeding of alpha-lipoic acid in diet is safe and effective. It improves the reduced glutathione (GSH) to oxidized glutathione (GSSG) ratio. The chronic administration of alpha-lipoic acid in the diet can be for periods of one, two, three, four, five, or six months minimum up through a period of one, two, three, four, five years or even more including the lifetime of the animal. The alpha-lipoic acid functions without any special protection in the diet such as encapsulation and need not be present in the diet in a unit dosage form such as those used in pharmaceuticals, for example, tablet, pill, capsule and the like. The lipoic acid is provided in the diet in a minimum of about 25, 50, 75, or 100 ppm of diet. The uppermost range is just below its toxic level, all the way down to about 400, 300, or 200 ppm of diet. Generally, one does not go beyond about 6 or 7 mg/kg body weight of animal per day, more generally not above about 5. The alpha-lipoic acid improves antioxidant defense capabilities as well as improves the animal's ability to resist oxidative damage. All this is done with the proper quantities of other antioxidants present such as vitamin E and vitamin C. This demonstrates that the action of alpha-lipoic acid is beyond that of vitamin C and/or vitamin E.

Example 3

Materials and Methods

Thirty (30) dogs were used to determine the effect of lipoic acid when compared to an AAFCO control food or a test food containing fish oil.

A differential gene expression profile was studied between an AAFCO control food, a food containing fish oil, and a food containing lipoic acid. At a minimum of 1.3 fold change, a list of 1212 genes was generated compared to the AAFCO control and 1896 genes compared to the food containing fish oil at d 30.

RNA Extraction:

Total RNAs were isolated from whole blood samples using the PAXgene RNA isolation kit. All measurements were done with the canine 2 Affymetrix genechips. For statistical analysis, all measurements were normalized with RMA. All analysis was preformed using Partek. An ANOVA t-test was performed for genes that are differentially expressed between the control and test foods were selected based on p-value cutoff 0.1, fold change>+/−1.3.

Gene Expression:

Expression of 1212 genes was found to be altered in dogs fed a test food containing 150 ppm lipoic acid when compared to dogs fed an AAFCO control food. In addition, expression of 1896 genes was found to be altered in dogs fed the test food containing lipoic acid compared to a test food containing fish oil. Table 9 shows the genes grouped by function and the direction of expression relative to those fed either the control food or a food containing fish oil.

Metabolomics:

Plasma metabolites were analyzed and were compared as fold change relative to the control fed dogs.

Biomarker Measurements:

Serum cartilage markers were measured using ELISA based kits to determine concentrations of cartilage markers. Day 0 was used as a covariate in the analysis to adjust for baseline values.

Results:

The addition of lipoic acid to a food resulted in a greater decrease in type II collagen C-propeptide and carboxy-terminal crosslinked telopeptide fragment of type II collagen than a similar food without lipoic acid. These two markers are known to increase in dogs with osteoarthritis. Additionally, dogs fed a food containing lipoic acid lost fat suggesting an increase in utilization of fat for energy (fat oxidation) and a decreased production of glucose for healthier weight maintenance. In other words, dogs fed lipoic acid utilized available glucose more efficiently and shifted their metabolism towards mobilization of fat for energy use. Additionally, the metabolite hydroxyproline was reduced in plasma suggesting reduced cartilage destruction as this metabolite almost exclusively originates from cartilage. Furthermore, changes in gene expression as determined from serum white blood cells support the evidence to suggest increased cartilage protection from increased synthesis of cartilage components and decreased expression of enzymes that degrade cartilage. Finally, gene expression changes suggest improved fat utilization by increasing PDK4, which inhibits the formation of pyruvate from glucose and shifts metabolism to shuttling acetyl-CoA for energy, and upregulation of glucose transporters. The dogs fed lipoic acid also appeared genomically leaner compared to dogs fed the control food.

The following tables show the difference in fat and weight as well as cartilage markers relative to treatment with lipoic acid.

Table 4 illustrates the change in body composition of dogs fed a control diet compared with dogs fed a control plus fish oil and a control plus lipoic acid. As illustrated in Table 4, dogs fed a control plus lipoic acid exhibited greatest change in weight over a 90 day treatment period.

TABLE 4

Change in body composition over 90 days.

| | Treatment | | | | | Probability, P < | | |
|---|---|---|---|---|---|---|---|---|
| | Control | Fish oil | Lipoic acid | SE | Treatment | Fish oil vs Control | Fish oil vs lipoic acid | control vs lipoic acid |
| Total weight, g | 14,400 | 14,500 | 13,800 | 414.0 | 0.17 | 0.79 | 0.08 | 0.14 |
| Change in weight, g | 44.4 | 160.4 | −637.5 | 414.56 | 0.14 | 0.78 | 0.07 | 0.11 |
| Total fat, g | 3245.6 | 3175.3 | 2788.3 | 281.01 | 0.23 | 0.80 | 0.18 | 0.11 |
| Change in fat, g | −61.2 | −66.6 | −587.2 | 313.79 | 0.18 | 0.99 | 0.11 | 0.11 |

Table 5 illustrates the change in pyruvate blood levels in of dogs fed a control diet compared with dogs fed a control plus fish oil and a control plus lipoic acid. As illustrated in Table 5, dogs fed a control plus lipoic acid exhibited greatest change in pyruvate blood levels over a 30 day treatment period.

TABLE 5

Fold change in pyruvate measured in the blood in dogs at day 30 fed three foods[a]

| | | | | Probability, P < | |
|---|---|---|---|---|---|
| Metabolite | Control | Lipoic acid vs Control | Lipoic acid vs Fish oil | +lipoic vs Control | +lipoic vs upgrade |
| Pyruvate | 1.000 | 0.5379 | 0.6274 | 0.01 | 0.03 |

[a]Day 0 values used as a covariate in the analysis.

Table 6 illustrates the percentage of dogs classified as genomically fat after being fed a control diet compared with dogs fed a control plus fish oil and a control plus lipoic acid for 30 days. As illustrated in Table 6, dogs fed a control plus lipoic acid genomically did not resemble physically fat dogs after a 30 day treatment period.

TABLE 6

Percentage of Animals Classifying Genomically Fat

| | | | | Probability, P < | |
|---|---|---|---|---|---|
| Measure % | Control | Fish Oil | Lipoic Acid | Lipoic Acid vs. Control | Lipoic Acid vs. Fish Oil |
| Percentage of animals at d 30 that classified fat using genomic markers | 30 | 10 | 0 | 0.08 | 0.33 |

Table 7 illustrates the change in blood level of arthritic markers in dogs after being fed a control diet compared with dogs fed a control plus fish oil and a control plus lipoic acid for 30 days and measured again at day 90. As illustrated in Table 7, dogs fed a control plus lipoic acid displayed reduction in arthritic markers (i.e., CPII and CTXII) after a 30 day treatment period and a greater reduction in arthritic markers after a 90 day period of being fed a control plus lipoic acid.

TABLE 7

Arthritic markers measured in the blood in dogs fed three different foods[a][b]

| | | | | | | Probability, P < | | |
|---|---|---|---|---|---|---|---|---|
| Metabolite | Control | Fish oil | Lipoic acid | SE | Treatment | Fish oil vs Control | Fish oil vs Lipoic acid | Lipoic acid vs Control |
| Day 30 | | | | | | | | |
| CPII, ng/mL | 1076.9 | 997.61 | 986.28 | 29.254 | 0.004 | 0.01 | 0.70 | 0.01 |
| Change CPII | 17.00 | −30.50 | −95.10 | 33.863 | 0.01 | 0.17 | 0.07 | 0.01 |
| Change CTXII | −2.33 | −0.03 | −5.60 | 2.622 | 0.12 | 0.39 | 0.04 | 0.22 |
| Day 90 | | | | | | | | |
| CPII, ng/mL | 941.1 | 897.8 | 848.0 | 33.56 | 0.02 | 0.18 | 0.15 | 0.01 |
| Change CPII | −118.70 | −131.00 | −232.70 | 36.546 | 0.01 | 0.74 | 0.01 | 0.01 |
| Change CTXII | −3.24 | −1.23 | −0.59 | 6.119 | 0.90 | 0.75 | 0.92 | 0.67 |

[a]Individual markers analyzed with d 0 as covariate

[b]Change in individual markers and ratios analyzed without covariates.

Table 8 illustrates the directional change (up regulation or down regulation) in genes related to cartilage metabolism in dogs after being fed a control diet compared with dogs fed a control plus fish oil and a control plus lipoic acid for 90 days in canine bone cells. As illustrated in Table 8, dogs fed a control plus lipoic acid displayed down regulation in MMP-3 gene corresponding to a degradation of the collagen component of cartilage, up-regulation of TIMP2 corresponding to inhibition of MMP's, and up-regulation of prolyl 4-hydroxylase, which corresponds to the rate limiting step in collagen type II synthesis (i.e., produces hydroxyproline for incorporation into collagen epitope.

TABLE 8

Genes related to cartilage metabolism altered by lipoic acid in canine bone cells

| Gene | Probe | Directional change | Function |
|---|---|---|---|
| MMP3 | 1582602_at | Down | Degradation of collagen component of cartilage |
| TIMP2 | 1582708_at | up | Inhibits MMPs |
| Prolyl 4-hydroxylase | 1600479_at | up | Rate limiting step in collagen type II synthesis, produces hydroxyproline for incorporation into collagen epitope |

Table 9 illustrates the change in genes related to cartilage metabolism and energy metabolism in dogs after being fed a control diet compared with dogs fed a control plus fish oil and a control plus lipoic acid for 90 days.

TABLE 9

Genes related to cartilage and energy metabolism altered by lipoic acid compared to the control or upgrade foods (upgrade contains fish oil)

| Gene name | Probe | Fold change | lipoic acid vs. |
|---|---|---|---|
| Related to cartilage metabolism | | | |
| Prolyl hydroxylase alpha 1 | CfaAffx.22481.1.S1_at | 1.4 | control |
| Prolyl hydroxylase alpha 2 | Cfa.13303.2.S1_a_at | 1.3 | control |
| Facilitated glucose transporter 9 | Cfa.7132.1.A1_at | 1.4 | control |
| TIMP1 | Cfa.3680.1.S1_s_at | 1.3 | control |
| Chondroitan sulfate Synthase 1 | CfaAffx.16537.1.S1_at | 1.4 | control |
| heparan sulfate N-deacetylase/N-sulfotransferase 2 | Cfa.11897.1.A1_at | 1.3 | control |
| 12-lipooxygenase | CfaAffx.25908.1.S1_s_at | −1.3 | control |
| chondroitan sulfate protcoglycan 2 (veriscan) | CfaAffx.13597.1.S1_s_at | 1.5 | control |
| Lysyl hydroxylase | Cfa.16732.1A1_at | 1.3 | fish oil |
| N-acetylgalactosaminyl-transferase 1 | Cfa.12862.1.S1_at | 1.3 | fish oil |
| Chondroitan sulfate synthase 1 | CfaAffx.16537.1.S1_at | 1.3 | fish oil |
| Fibronectin 1 | Cfa.3707.2.S1_at | 1.4 | fish oil |
| chondroitan sulfate proteoglycan 2 (veriscan) | CfaAffx.13597.1.S1_s_at | 1.5 | fish oil |
| ADAMTS-2 | Cfa.6326.1.A1_x_at | −1.3 | fish oil |
| ADAMTS-10 | | −1.3 | fish oil |
| ADAMTS-16 | CfaAffx.16270.1.S1_at | −1.3 | fish oil |
| 12-lipooxygenase | CfaAffx.25908.1.S1_s_at | −1.3 | fish oil |
| MMP2 | CfaAffx.14851.1.S1_at | −1.3 | fish oil |
| MMP7 | CfaAffx.23201.1.S1_at | −1.3 | fish oil |
| Transforming growth factor beta receptor 1 | Cfa.13340.1.A1_at | 1.3 | fish oil |
| Facilitated glucose transporter 9 | Cfa.7132.1.A1_at | 1.4 | fish oil |
| Related to energy metabolism | | | |
| PDK4 | Cfa.2282.1.S1_at Cfa.19125.2.S1_at, | 1.4 | control |
| Hexokinase 3 | CfaAffx.25391.1.S1_s_at | 1.3 | control |
| 5' AMP alpha 1 | Cfa.9738.1.S1_s_at | 1.3 | control |
| 5' AMP beta 1 | CfaAffx.15678.1.S1_at | 1.3 | control |
| 5' AMP gamma 2 | Cfa.10276.2.S1_a_at, | 1.4 | control |
| Facilitated glucose transporter 1 | CfaAffx.4630.1.S1_s_at | 1.3 | control |
| Facilitated glucose transporter 6 | Cfa.6832.1.A1_at | 1.3 | control |
| Succinyl CoA ligase alpha | Cfa.16185.1.S1_at | 1.3 | control |
| PPAR gamma | CfaAffx.8402.1.S1_s_at | 1.3 | control |
| Fatty acid desaturase 1 | CfaAffx.24518.1.S1_at | 1.9 | control |
| cAMP responsice element modulator | Cfa.855.1.S1_at | 1.3 | fish oil |
| PDK4 | Cfa.2282.1.S1_at Cfa.19125.2.S1_at, | 1.6 | fish oil |
| Hexokinase 3 | CfaAffx.25391.1.S1_s_at | 1.3 | fish oil |
| 5' AMP alpha 1 | Cfa.9738.1.S1_s_at | 1.3 | fish oil |
| 5' AMP beta 1 | CfaAffx.15678.1.S1_at | 1.3 | fish oil |
| 5' AMP gamma 2 | Cfa.10276.2.S1_a_at, | 1.5 | fish oil |
| Facilitated glucose transporter 1 | CfaAffx.4630.1.S1_s_at | 1.3 | fish oil |
| Facilitated glucose transporter 6 | Cfa.6832.1.A1_at | 1.4 | fish oil |
| Succinyl CoA ligase alpha | Cfa.16185.1.S1_at | 1.3 | fish oil |
| Succinyl CoA ligase beta | Cfa.1485.1.S1_at | 1.3 | fish oil |
| PPAR gamma | CfaAffx.8402.1.S1_s_at | 1.3 | fish oil |
| SREBP-1 | Cfa.189.2.S1_s_at | −1.3 | fish oil |

Table 10 illustrates the ingredients in an illustrative pet food composition of the invention.

TABLE 10

Ingredients used to make composition

| | Ingredients |
|---|---|
| 1 | Wheat |
| 2 | Milo |
| 3 | Corn |
| 4 | Ground Chicken |
| 5 | Corn Gluten Meal |
| 6 | Poultry Meal |

TABLE 10-continued

Ingredients used to make composition

| | Ingredients |
|---|---|
| 7 | Soy bean oil |
| 8 | Flaxseed |
| 9 | Rice Brewers |
| 10 | Soybean meal, 49% |
| 11 | Pal enhancer 1 |
| 12 | Beet pulp |
| 13 | Potassium Citrate |
| 14 | Fish oil |
| 15 | DL-methionine |
| 16 | L-lysine HCl |
| 17 | Salt |
| 18 | Calcium carbonate |
| 19 | Lipoic acid |
| 20 | Choline chloride |
| 21 | Vitamin premix |
| 22 | L-threonine |
| 23 | Vitamin E |
| 24 | L-tryptophan |
| 25 | Lipoic acid |
| 26 | Mineral premix |
| 27 | Preservative |

Table 11 illustrates immune status makers in blood samples for dogs after being fed a control diet compared with dogs fed a control plus lipoic acid for 90 days. As illustrated in Table 11, dogs fed a food including lipoic acid displayed increased immune status markers after 90 days.

TABLE 11

Immune status markers measured in the blood in dogs at day 90.

| | | | | | Probability, $P <$ | | |
|---|---|---|---|---|---|---|---|
| Metabolite | Control | Upgrade | Upgrade + lipoic acid | SE | Upgrade vs Control | Upgrade vs lipoic | control vs lipoic |
| Vitamin E, μg/mL | 24.15 | 30.47 | 34.51 | 3.318 | 0.07 | 0.23 | 0.01 |
| Vitamin E: Cholesterol | 0.29 | 0.51 | 0.55 | 0.074 | 0.01 | 0.67 | 0.01 |
| Vitamin E: Triglyceride | 0.14 | 0.17 | 0.17 | 0.009 | 0.01 | 0.62 | 0.01 |

*Day 0 values used as a covariate in the analysis
Control refers to standard AAFCO dog food.
Upgrade refers to a low fat, reduced calorie, high fiber pet food.

Table 12 illustrates arthritic makers measured in blood samples for dogs after being fed a control diet compared with dogs fed a pet food including lipoic acid for 90 days. As illustrated in Table 12, dogs fed a control plus lipoic acid displayed decreased immune status markers after 90 days.

TABLE 12

Arthritic markers measured in the blood in dogs at day 90 fed different foods[a][b]

| | | | | | Probability, $P <$ | | |
|---|---|---|---|---|---|---|---|
| Metabolite | Control | Upgrade | Upgrade + lipoic | SE | Upgrade vs Control | Upgrade vs + lipoic | control vs + lipoic |
| CPII, ng/mL | 941.1 | 897.8 | 848.0 | 33.56 | 0.18 | 0.15 | 0.01 |
| COMP, U/L | 1.77 | 1.96 | 1.86 | 0.088 | 0.04 | 0.28 | 0.30 |
| CPII:COMP ratio | 535.3 | 460.4 | 483.3 | 41.78 | 0.08 | 0.59 | 0.22 |
| Change CPII | −118.70 | −131.00 | −232.70 | 36.546 | 0.74 | 0.01 | 0.01 |
| Change COMP | −1.53 | −1.31 | −1.39 | 0.153 | 0.17 | 0.60 | 0.39 |
| Eicosapentaenoic Acid, mg/dL | 0.15 | 9.88 | 10.4 | 1.259 | 0.01 | 0.69 | 0.01 |

[a]Individual markers analyzed with d 0 as covariate
[b]Change in individual markers and ratios analyzed without covariates.
Control refers to standard AAFCO dog food.
Upgrade refers to a low fat, reduced calorie, high fiber pet food.

Table 13 illustrates skin and coat makers measured in blood samples for dogs after being fed a control diet compared with dogs fed a pet food including lipoic acid for 90 days. As illustrated in Table 13, dogs fed a control plus lipoic acid displayed increased skin and coat markers after 90 days.

TABLE 13

Skin and coat markers measured in the blood in dogs at day 90.

| Metabolite | Control | Upgrade | Upgrade + lipoic | SE | Probability, P < | | |
| --- | --- | --- | --- | --- | --- | --- | --- |
| | | | | | Upgrade vs Control | Upgrade vs + lipoic | control vs + lipoic |
| Vitamin E, µg/mL | 24.15 | 30.47 | 34.51 | 3.318 | 0.07 | 0.23 | 0.01 |
| Vitamin E: Cholesterol | 0.29 | 0.51 | 0.55 | 0.074 | 0.01 | 0.67 | 0.01 |
| Vitamin E: Triglyceride | 0.14 | 0.17 | 0.17 | 0.009 | 0.01 | 0.62 | 0.01 |
| Linoleic Acid, mg/dL | 55.22 | 61.51 | 66.02 | 5.062 | 0.23 | 0.38 | 0.04 |
| Eicosapentaenoic Acid, mg/dL | 0.15 | 9.88 | 10.4 | 1.259 | 0.01 | 0.69 | 0.01 |
| Docosahexaenoic Acid, mg/dL | 1.38 | 11.07 | 11.56 | 1.419 | 0.01 | 0.74 | 0.01 |
| Arachodonic acid, mg/dL | 54.57 | 34.65 | 37.67 | 5.074 | 0.01 | 0.56 | 0.01 |

*Day 0 values used as a covariate in the analysis.
Control refers to standard AAFCO dog food.
Upgrade refers to a low fat, reduced calorie, high fiber pet food.

Table 14 illustrates kidney makers measured in blood samples for dogs after being fed a control diet compared with dogs fed a pet food including lipoic acid for 90 days. As illustrated in Table 14, dogs fed a control plus lipoic acid displayed decreased kidney markers after 90 days.

TABLE 14

Kidney markers measured in the blood in dogs at day 90 fed three foods

| Metabolite | Control | Upgrade | Upgrade + lipoic | SE | Probability, P < | | |
| --- | --- | --- | --- | --- | --- | --- | --- |
| | | | | | Upgrade vs Control | Upgrade vs + lipoic | +lipoic vs control |
| Urine specific gravity | 1.026 | 1.025 | 1.027 | 0.005 | 0.84 | 0.58 | 0.73 |
| Blood Urea Nitrogen: Creatinine | 16.42 | 22.76 | 22.84 | 2.472 | 0.02 | 0.98 | 0.01 |
| Blood Urea Nitrogen, mg/dL | 11.71 | 14.31 | 13.54 | 1.525 | 0.10 | 0.62 | 0.23 |
| Creatinine, mg/dL | 0.69 | 0.64 | 0.61 | 0.024 | 0.03 | 0.24 | 0.01 |

*Day 0 values used as a covariate in the analysis.
Control refers to standard AAFCO dog food.
Upgrade refers to a low fat, reduced calorie, high fiber pet food Table 15 illustrates Dual Energy X-Ray Absorptiometry (DEXA) measurement for dogs after being fed a control diet compared with dogs fed a pet food including lipoic acid for 90 days. The measurement of body fat using DEXA is more accurate than body weight for assessing health. A dog can have a lot of muscle, but be considered "over-weight" by many height/weight charts. The opposite can also be true—a dog can have a lot of fat and little muscle and be "over-fat" but not overweight.

TABLE 15

Canine Nutrigenomics DEXA (Dual Energy X-Ray Absorptiometry) at day 90 with initial as covariate

| | Treatment | | | | Probability, P < | | |
| --- | --- | --- | --- | --- | --- | --- | --- |
| | Control | Upgrade | Upgrade + lipoic | SE | Upgrade vs Control | Upgrade vs + lipoic | control vs + lipoic |
| Total weight, kg | 14.4 | 14.5 | 13.8 | 0.41 | 0.79 | 0.08 | 0.14 |
| Food intake, g | 303.1 | 306.4 | 269.9 | 25.963 | 0.90 | 0.17 | 0.21 |
| Body condition score | 3.3 | 3.2 | 3.2 | 0.198 | 0.62 | 0.99 | 0.62 |
| BMC, g | 474.1 | 477.61 | 464.5 | 6.981 | 0.62 | 0.07 | 0.18 |
| BMD, g | 0.89 | 0.90 | 0.88 | 0.012 | 0.43 | 0.20 | 0.61 |
| lean, g | 10699 | 10820 | 10558 | 220.73 | 0.59 | 0.25 | 0.53 |
| % fat | 21.54 | 21.59 | 20.69 | 1.643 | 0.98 | 0.59 | 0.61 |
| Total fat, g | 3245.6 | 3175.3 | 2788.3 | 281.01 | 0.80 | 0.18 | 0.11 |
| Lean:fat ratio | 4.15 | 4.20 | 4.25 | 0.425 | 0.90 | 0.92 | 0.82 |
| BMC, % | 3.3 | 3.3 | 3.3 | 0.10 | 0.78 | 0.67 | 0.48 |
| % lean | 74.8 | 75.4 | 76.4 | 1.50 | 0.67 | 0.48 | 0.26 |

*Day 0 used as a covariate
Control refers to standard AAFCO dog food.
Upgrade refers to a low fat, reduced calorie, high fiber pet food Table 16 illustrates immune status and antioxidant makers measured in blood samples for dogs after being fed five different foods for 180 days.

TABLE 16

Immune status and antioxidant markers measured in the blood in dogs at day 180 fed five different foods*

| | | | | | | | Probability, P < | | | |
| --- | --- | --- | --- | --- | --- | --- | --- | --- | --- | --- |
| Metabolite | #1 | #2 | #3 | #4 | #5 | SE | vs #1 | vs #2 | vs #4 | vs #5 |
| Glutathionine peroxidase, μg/10$^6$ | 5.44 | 5.96 | 5.74 | 5.65 | 5.35 | 0.401 | NS | NS | NS | NS |
| Vitamin E, μg/mL | 28.65 | 37.03 | 29.5 | 41.24 | 23.35 | 2.377 | NS | 0.05 | 0.05 | 0.05 |
| Vitamin E: Cholesterol | 0.15 | 0.20 | 0.15 | 0.20 | 0.13 | 0.009 | NS | 0.05 | 0.05 | 0.05 |
| Vitamin E: Triglyceride | 0.27 | 0.29 | 0.31 | 0.37 | 0.19 | 0.062 | NS | NS | NS | NS |

*Day 0 used as a covariate
Control refers to standard AAFCO dog food.
Upgrade refers to a low fat, reduced calorie, high fiber pet food Table 17 illustrates arthritic makers measured in blood samples for dogs after being fed five different foods for 180 days.

TABLE 17

Arthritic markers measured in the blood in dogs at day 180 fed five different foods*

| | | | | | | | Probability, P < | | | |
| --- | --- | --- | --- | --- | --- | --- | --- | --- | --- | --- |
| Metabolite | #1 | #2 | #3 | #4 | #5 | SE | vs #1 | vs #2 | Vs #4 | vs #5 |
| Osteocalcin, ng/mL | 6.81 | 8.64 | 9.53c | 8.29 | 6.71 | 0.883 | 0.05 | NS | NS | 0.05 |
| Cartilage Oligomeric Matrix Protein, U/L | 3.17 | 3.30 | 3.23 | 3.19 | 3.38 | 0.204 | NS | NS | NS | NS |
| Amino Terminal Crosslink Telopeptide, nM BCE | 21.42 | 25.53 | 24.89 | 24.02 | 23.63 | 2.707 | NS | NS | NS | NS |

TABLE 17-continued

Arthritic markers measured in the blood in dogs at day 180 fed five different foods*

| Metabolite | #1 | #2 | #3 | #4 | #5 | SE | Probability, P < | | | |
|---|---|---|---|---|---|---|---|---|---|---|
| | | | | | | | vs #1 | vs #2 | Vs #4 | vs #5 |
| Eicosapentaenoic Acid, mg/dL | 1.88b | 0.49a | 8.07c | 1.79b | 0.47 | 0.388 | 0.05 | 0.05 | 0.05 | 0.05 |

*Day 0 used as a covariate

Table 18 illustrates skin and coat makers measured in blood samples for dogs after being fed five different dog foods for 180 days.

TABLE 18

Skin and coat markers measured in the blood in dogs at day 180 fed five different foods

| Metabolite | #1 | #2 | #3 | #4 | #5 | SE | Probability, P < | | | |
|---|---|---|---|---|---|---|---|---|---|---|
| | | | | | | | vs #1 | vs #2 | Vs #4 | vs #5 |
| Vitamin E, μg/mL | 28.65 | 37.03 | 29.5 | 41.24 | 23.35 | 2.377 | NS | 0.05 | 0.05 | 0.05 |
| Vitamin E: Cholesterol | 0.15 | 0.20 | 0.15 | 0.20 | 0.13 | 0.009 | NS | 0.05 | 0.05 | 0.05 |
| Vitamin E: Triglyceride | 0.27 | 0.29 | 0.31 | 0.37 | 0.19 | 0.062 | NS | NS | NS | NS |
| Linoleic Acid, mg/dL | 51.67 | 53.84 | 62.23 | 50.13 | 51.98 | 2.966 | 0.05 | 0.05 | 0.05 | 0.05 |
| Eicosapentaenoic Acid, mg/dL | 1.88 | 0.49 | 8.07 | 1.79 | 0.47 | 0.388 | 0.05 | 0.05 | 0.05 | 0.05 |
| Docosahexaenoic Acid, mg/dL | 10.36 | 2.68 | 13.43 | 11.86 | 2.01 | 0.646 | 0.05 | 0.05 | 0.05 | 0.05 |

Table 19 illustrates kidney makers measured in blood samples for dogs after being fed five different pet foods for 180 days.

TABLE 19

Kidney markers measured in the blood in dogs at day 180 fed five different foods

| Metabolite | #1 | #2 | #3 | #4 | #5 | SE | Probability, P < | | | |
|---|---|---|---|---|---|---|---|---|---|---|
| | | | | | | | vs #1 | vs #2 | Vs #4 | vs #5 |
| Urine specific gravity | 1.032 | 1.028 | 1.032 | 1.032 | 1.032 | 0.0047 | NS | NS | NS | NS |
| ERD (healthy (0) vs unhealthy (1, 2, 3) count) | 0 | 1 | 0 | 2 | 0 | — | NS | NS | NS | NS |
| Blood Urea Nitrogen: Creatinine | 18.78 | 19.50 | 19.86 | 21.12 | 19.38 | 1.070 | NS | NS | NS | NS |
| Blood Urea Nitrogen, mg/dL | 14.03 | 14.64 | 14.27 | 16.22 | 13.54 | 0.831 | NS | NS | 0.05 | NS |
| Creatinine, mg/dL | 0.75 | 0.75 | 0.72 | 0.78 | 0.70 | 0.034 | NS | NS | NS | NS |

*Day 0 values used as a covariate in the analysis.

Table 20 illustrates body composition at day 180 to determine treatment effect with initial covariate for dogs fed five different pet foods for 180 days.

TABLE 20

| | Canine body composition at day 180 Adult treatment effect with initial covariate | | | | | | | | | |
|---|---|---|---|---|---|---|---|---|---|---|
| | Treatment | | | | | | Probability, P < | | | |
| | #1 | #2 | #3 | #4 | #5 | SE | vs #1 | vs #2 | Vs #4 | vs #5 |
| BMC, g | 419.78 | 395.51 | 400.1 | 442.07 | 393.07 | 24.95 | 0.05 | NS | NS | 0.05 |
| BMD, g | 0.601 | 0.584 | 0.587 | 0.623 | 0.577 | 0.0185 | NS | NS | NS | 0.05 |
| lean | 7929 | 7631 | 7758 | 7982 | 7380 | 479.6 | NS | NS | NS | NS |
| % fat | 24.2 | 25.50 | 26.5 | 28.8 | 27.20 | 2.480 | NS | NS | NS | NS |
| Total fat | 2726 | 2843 | 3012 | 3361 | 2945 | 365.6 | NS | NS | NS | NS |
| Total weight, kg | 11.1 | 10.9 | 11.2 | 11.8 | 10.7 | 681.3 | NS | NS | NS | NS |
| Lean:fat ratio | 3.28 | 3.01 | 2.86 | 2.57 | 2.95 | 0.405 | NS | NS | NS | NS |
| % BMC | 3.85 | 3.73 | 3.67 | 3.78 | 3.74 | 0.101 | NS | NS | NS | NS |
| % lean | 72.9 | 72.3 | 71.1 | 68.0 | 70.6 | 2.60 | NS | NS | NS | NS |

Table 21 illustrates blood cytokine levels at day 180 to determine treatment effect with initial covariate for dogs fed five different pet foods for 180 days.

TABLE 21

| | Canine blood cytokine levels at d 180 with d 0 as covariate | | | | | | | | | |
|---|---|---|---|---|---|---|---|---|---|---|
| | | | | | | | Probability, P < | | | |
| Measure | #1 | #2 | #3 | #4 | #5 | SE | vs #1 | vs #2 | Vs #4 | vs #5 |
| IL-2 (pg/ml) | 635.2 | 251.60 | 263.9 | 371.00 | 257.10 | 394.21 | 0.20 | 0.97 | 0.98 | 0.77 |
| IL-6 (pg/ml) | 103.7 | 66.8 | 45.9 | 41.7 | 66.50 | 48.606 | 0.11 | 0.55 | 0.55 | 0.93 |
| IL-7 (pg/ml) | 369.0 | 235.9 | 215.7 | 661.6 | 210.4 | 200.49 | 0.30 | 0.89 | 0.97 | 0.02 |
| IL-8 (pg/ml) | 989.8 | 885.0 | 1024.3 | 1261.1 | 833.3 | 227.10 | 0.82 | 0.37 | 0.21 | 0.24 |
| IL-15 (pg/ml) | 477.8 | 390.8 | 280.5 | 476.0 | 374.7 | 247.07 | 0.28 | 0.53 | 0.59 | 0.39 |
| IL-18 (pg/ml) | 458.7 | 200.6 | 172.4 | 297.5 | 262.5 | 238.53 | 0.10 | 0.87 | 0.60 | 0.57 |
| KC (pg/ml) | 803.6 | 643.6 | 653.9 | 592.6 | 589.0 | 105.65 | 0.05 | 0.89 | 0.38 | 0.54 |
| MCP-1 (pg/ml) | 349.2 | 216.8 | 215.4 | 223.7 | 256.2 | 108.13 | 0.09 | 0.99 | 0.60 | 0.93 |
| IP-10 (pg/ml) | 6.05 | 7.93 | 3.98 | 7.76 | 2.89 | 3.572 | 0.41 | 0.12 | 0.68 | 0.25 |
| IFN-gamma (pg/ml) | 31.88 | 29.61 | 15.07 | 9.03 | 19.79 | 25.207 | 0.36 | 0.42 | 0.79 | 0.80 |
| GM-CSF (pg/ml) | 620.9 | 217.2 | 223.7 | 351.8 | 284.2 | 301.51 | 0.08 | 0.98 | 0.78 | 0.65 |
| Total Pro-inflammatory cytokines | 5351.1 | 2394.10 | 2832.2 | 4535.5 | 3284.1 | 1482.30 | 0.02 | 0.70 | 0.68 | 0.22 |

Table 22 illustrates change in metabolite measured in blood samples for dogs after being fed a control diet compared with dogs fed a pet food including lipoic acid for 30 days. As illustrated in Table 22, dogs fed a control plus lipoic acid displayed decreased kidney markers after 30 days.

TABLE 22

| | Fold change in metabolites measured in the blood in dogs at day 30 fed three foods[a] | | | | |
|---|---|---|---|---|---|
| | | | | Probability, P < | |
| Metabolite | Control | Upgrade vs Control | Upgrade vs Fish oil | Upgrade vs Control | Upgrade vs fish oil |
| Pyruvate | 1.0 | 0.54 | 0.63 | 0.01 | 0.03 |
| Hydroxyproline | 1.0 | 0.54 | 0.90 | 0.01 | 0.22 |
| 3-Indoxylsulfuric acid | 1.0 | 0.49 | 0.85 | 0.10 | 0.78 |
| 1,5 anhydrosorbitol | 1.0 | 0.75 | 1.10 | 0.01 | 0.33 |
| Nervonic acid | 1.0 | 1.40 | 1.05 | 0.01 | 0.24 |
| Alpha-tocopherol | 1.0 | 1.30 | 0.96 | 0.01 | 0.88 |

TABLE 22-continued

Fold change in metabolites measured in the blood in dogs at day 30 fed three foods[a]

| Metabolite | Control | Upgrade vs Control | Upgrade vs Fish oil | Probability, P < Upgrade vs Control | Upgrade vs fish oil |
|---|---|---|---|---|---|
| Coenzyme Q10 | 1.0 | 1.84 | 1.29 | 0.01 | 0.13 |
| Allantoin | 1.0 | 0.97 | 1.25 | 0.78 | 0.02 |
| Creatine | 1.0 | 0.78 | 1.50 | 0.06 | 0.20 |
| Taurine | 1.0 | 1.41 | 0.98 | 0.01 | 0.98 |

[a]Day 0 values used as a covariate in the analysis.
Control refers to standard AAFCO dog food.
Upgrade refers to a low fat, reduced calorie, high fiber pet food The invention is not to be limited in scope by the specific embodiments disclosed in the examples, which are intended as illustrations of a few aspects of the invention, and any embodiments, which are functionally equivalent, are within the scope of this invention. Indeed, various modifications of the invention in addition to those shown and described herein will become apparent to those skilled in the art and are intended to fall within the appended claims.

For any references that have been cited, the entire disclosures of which are incorporated herein by reference.

What is claimed is:

1. A pet food composition comprising an effective amount of lipoic acid to treat a degenerative joint condition in a companion animal in need thereof, wherein said effective amount of lipoic acid to prevent or treat a degenerative joint condition is at least 25 ppm to about 600 ppm, the pet food composition further comprising vitamin E at a level of 500-1000 ppm, vitamin C at levels of 100-200 ppm, and fat, carbohydrate, protein, and dietary fiber to form a pet food.

2. The composition of claim 1, wherein the amount of lipoic acid is at least 50 ppm.

3. The composition of claim 1, wherein the amount of lipoic acid is at least 100 ppm.

4. The composition of claim 1, wherein the amount of lipoic acid is about 100 ppm to about 600 ppm.

5. The composition of claim 1, wherein the amount of lipoic acid is about 100 ppm to about 200 ppm.

6. The composition of claim 1, wherein the companion animal is a dog.

7. The composition of claim 1, wherein the companion animal is a cat.

8. The composition of claim 1, wherein the degenerative joint condition comprises osteoarthritis.

9. The composition of claim 1, wherein the degenerative joint condition comprises cartilage damage.

10. A pet food composition comprising an effective amount of lipoic acid to modulate enzymatic degradation of articular cartilage in a companion animal in need thereof, wherein said effective amount of lipoic acid to modulate enzymatic degradation of articular cartilage is at least 25 ppm to about 600 ppm, the pet food composition further comprising vitamin E at a level of 500-1000 ppm, vitamin C at levels of 100-200 ppm, and fat, carbohydrate, protein, and dietary fiber to form a pet food.

11. The composition of claim 10, wherein the amount of lipoic acid is at least 50 ppm.

12. The composition of claim 10, wherein the amount of lipoic acid is at least 100 ppm.

13. The composition of claim 10, wherein the amount of lipoic acid is about 100 ppm to about 600 ppm.

14. The composition of claim 10, wherein the amount of lipoic acid is about 100 ppm to about 200 ppm.

15. The composition of claim 10, wherein the companion animal is a dog.

16. The composition of claim 10, wherein the companion animal is a cat.

17. A pet food composition comprising an effective amount of lipoic acid to maintain or increase bone mineral density in a companion animal in need thereof, wherein said effective amount of lipoic acid to maintain or increase bone mineral density is at least 25 ppm to about 600 ppm, the pet food composition further comprising vitamin E at a level of 500-1000 ppm, vitamin C at levels of 100-200 ppm, and fat, carbohydrate, protein, and dietary fiber to form a pet food.

18. The composition of claim 17, wherein the amount of lipoic acid is at least 50 ppm.

19. The composition of claim 17, wherein the amount of lipoic acid is at least 100 ppm.

20. The composition of claim 17, wherein the amount of lipoic acid is about 100 ppm to about 600 ppm.

21. The composition of claim 17, wherein the amount of lipoic acid is about 100 ppm to about 200 ppm.

22. The composition of claim 17, wherein the companion animal is a dog.

23. The composition of claim 17, wherein the companion animal is a cat.

24. A pet food composition comprising an effective amount of lipoic acid treat kidney-related disorders in a companion animal in need thereof, wherein said effective amount of lipoic acid to prevent or treat kidney-related disorders is at least 25 ppm to about 600 ppm, the pet food composition further comprising vitamin E at a level of 500-1000 ppm, vitamin C at levels of 100-200 ppm, and fat, carbohydrate, protein, and dietary fiber to form a pet food.

25. The composition of claim 24, wherein the amount of lipoic acid is at least 50 ppm.

26. The composition of claim 24, wherein the amount of lipoic acid is at least 100 ppm.

27. The composition of claim 24, wherein the amount of lipoic acid is about 100 ppm to about 600 ppm.

28. The composition of claim 24, wherein the amount of lipoic acid is about 100 ppm to about 200 ppm.

29. The composition of claim 24, wherein the companion animal is a dog.

30. The composition of claim 24, wherein the companion animal is a cat.

31. A pet food composition comprising an effective amount of lipoic acid to enhance palatability to a companion animal in need thereof, wherein said effective amount of lipoic acid to enhance palatability is at least 25 ppm to about 600 ppm, the pet food composition further comprising vitamin E at a level of 500-1000 ppm, vitamin C at levels of 100-200 ppm, and fat, carbohydrate, protein, and dietary fiber to form a pet food.

32. The composition of claim 31, wherein the amount of lipoic acid is at least 50 ppm.

33. The composition of claim 31, wherein the amount of lipoic acid is at least 100 ppm.

34. The composition of claim 31, wherein the amount of lipoic acid is about 100 ppm to about 600 ppm.

35. The composition of claim 31, wherein the amount of lipoic acid is about 100 ppm to about 200 ppm.

36. The composition of claim 31, wherein the companion animal is a dog.

37. The composition of claim 31, wherein the companion animal is a cat.

38. A pet food composition comprising an effective amount of lipoic acid to maintain or promote a healthy body composition in a companion animal in a companion animal in need thereof, wherein said effective amount of lipoic acid to maintain or promote a healthy body composition in a companion animal is at least 25 ppm to about 600 ppm, the pet food composition further comprising vitamin E at a level of 500-1000 ppm, vitamin C at levels of 100-200 ppm, and fat, carbohydrate, protein, and dietary fiber to form a pet food.

39. The composition of claim 38, wherein the amount of lipoic acid is at least 50 ppm.

40. The composition of claim 38, wherein the amount of lipoic acid is at least 100 ppm.

41. The composition of claim 38, wherein the amount of lipoic acid is about 100 ppm to about 600 ppm.

42. The composition of claim 38, wherein the amount of lipoic acid is about 100 ppm to about 200 ppm.

43. The composition of claim 38, wherein the companion animal is a dog.

44. The composition of claim 38, wherein the companion animal is a cat.

45. A pet food composition comprising an effective amount of lipoic acid to induce weight loss in a companion animal in need thereof, wherein said effective amount of lipoic acid to induce weight loss in a companion animal is at least 25 ppm to about 600 ppm, the pet food composition further comprising vitamin E at a level of 500-1000 ppm, vitamin C at levels of 100-200 ppm, and fat, carbohydrate, protein, and dietary fiber to form a pet food.

46. The composition of claim 45, wherein the amount of lipoic acid is at least 50 ppm.

47. The composition of claim 45, wherein the amount of lipoic acid is at least 100 ppm.

48. The composition of claim 45, wherein the amount of lipoic acid is about 100 ppm to about 600 ppm.

49. The composition of claim 45, wherein the amount of lipoic acid is about 100 ppm to about 200 ppm.

50. The composition of claim 45, wherein the companion animal is a dog.

51. The composition of claim 45, wherein the companion animal is a cat.

52. A pet food composition comprising an effective amount of lipoic acid to increase the percentage of lean muscle mass in a companion animal in need thereof, wherein said effective amount of lipoic acid to increase the percentage of lean muscle mass in a companion animal is at least 25 ppm to about 600 ppm, the pet food composition further comprising vitamin E at a level of 500-1000 ppm, vitamin C at levels of 100-200 ppm, and fat, carbohydrate, protein, and dietary fiber to form a pet food.

53. The composition of claim 52, wherein the amount of lipoic acid is at least 50 ppm.

54. The composition of claim 52, wherein the amount of lipoic acid is at least 100 ppm.

55. The composition of claim 52, wherein the amount of lipoic acid is about 100 ppm to about 600 ppm.

56. The composition of claim 52, wherein the amount of lipoic acid is about 100 ppm to about 200 ppm.

57. The composition of claim 52, wherein the companion animal is a dog.

58. The composition of claim 52, wherein the companion animal is a cat.

59. A pet food composition comprising an effective amount of lipoic acid wherein said effective amount of lipoic acid is at least 25 ppm to about 600 ppm, the pet food composition further comprising vitamin E at a level of 500-1000 ppm, vitamin C at levels of 100-200 ppm, and fat, carbohydrate, protein, and dietary fiber to form a pet food.

60. The composition of claim 59, wherein the amount of lipoic acid is at least 50 ppm.

61. The composition of claim 59, wherein the amount of lipoic acid is at least 100 ppm.

62. The composition of claim 59, wherein the amount of lipoic acid is about 100 ppm to about 600 ppm.

63. The composition of claim 59, wherein the amount of lipoic acid is about 100 ppm to about 200 ppm.

64. The composition of claim 59, wherein the companion animal is a dog.

65. The composition of claim 59, wherein the companion animal is a cat.

66. The composition of claim 59, wherein the composition is useful for treatment of detrimental conditions in a companion animal in need thereof.

67. The composition of claim 66, wherein the detrimental conditions comprise degenerative joint condition, modulation of enzymatic degradation of articular cartilage, maintenance or decrease bone mineral density, kidney-related disorders, reduced palatability, unhealthy body composition, obesity, decreased percentage of lean muscle mass in a companion animal in need thereof.

68. The composition of claim 67, wherein the degenerative joint condition comprises osteoarthritis.

69. The composition of claim 67, wherein the degenerative joint condition comprises cartilage damage.

70. The composition of claim 67, where the obesity is treated or prevented by inducing weight loss in the companion animal.

* * * * *